United States Patent
Boyce et al.

(10) Patent No.: US 7,467,153 B2
(45) Date of Patent: Dec. 16, 2008

(54) METHOD AND SYSTEM FOR EFFICIENT COLLECTION AND STORAGE OF EXPERIMENTAL DATA

(75) Inventors: Keith Boyce, Wexford, PA (US); Brian McKenna, Pittsburgh, PA (US); Phillip Glick, Cheswick, PA (US); Terry Dunlay, Plum Boro, PA (US)

(73) Assignee: Cellomics, Inc., Pittsburgh, PA (US)

( * ) Notice: Subject to any disclaimer, the term of this patent is extended or adjusted under 35 U.S.C. 154(b) by 306 days.

(21) Appl. No.: 10/649,323

(22) Filed: Aug. 27, 2003

(65) Prior Publication Data

US 2004/0139103 A1    Jul. 15, 2004

Related U.S. Application Data

(63) Continuation of application No. 09/437,976, filed on Nov. 10, 1999, now abandoned.

(60) Provisional application No. 60/142,375, filed on Jul. 6, 1999, provisional application No. 60/142,646, filed on Jul. 6, 1999, provisional application No. 60/140,240, filed on Jun. 21, 1999, provisional application No. 60/110,643, filed on Dec. 1, 1998, provisional application No. 60/108,291, filed on Nov. 13, 1998.

(51) Int. Cl.
  *G06F 17/40* (2006.01)
  *G06K 9/00* (2006.01)

(52) U.S. Cl. .................. 707/102; 707/104.1; 707/200; 382/131

(58) Field of Classification Search .................. 707/10, 707/200, 101, 102, 104.1; 709/203, 218; 382/131, 128, 164; 600/416
See application file for complete search history.

(56) References Cited

U.S. PATENT DOCUMENTS 4,857,549 A * 8/1989 Hill et al. .................... 514/495

(Continued)

FOREIGN PATENT DOCUMENTS

EP    0 367 544 A2    10/1989

(Continued)

OTHER PUBLICATIONS

Nathan Goodman, *The Fundamental Principles for Constructing a Successful Biological Laboratory Informatics System*, Scientific Computing & Automation, Jul. 1996, pp. 29-36.

(Continued)

*Primary Examiner*—Shahid A Alam
(74) *Attorney, Agent, or Firm*—Workman Nydegger

(57) ABSTRACT

Methods and system for efficient collection and storage of experimental data allow experimental data from high-throughput, feature-rich data collection systems, such as high-throughput cell data collection systems to be efficiently collected, stored, managed and displayed. The methods and system can be used, for example, for storing, managing, and displaying cell image data and cell feature data collected from microplates including multiple wells and a variety of biochips in which an experimental compound has been applied to a population of cells. The methods and system provide a flexible and scalable repository of experimental data including multiple databases at multiple locations including pass-through databases that can be easily managed and allows cell data to be analyzed, manipulated and archived. The methods and system may improve the identification, selection, validation and screening of new drug compounds that have been applied to populations of cells.

19 Claims, 14 Drawing Sheets

U.S. PATENT DOCUMENTS

| | | | |
|---|---|---|---|
| 4,942,526 A | 7/1990 | Okajima et al. | |
| 5,021,220 A | 6/1991 | Mertens | |
| 5,048,109 A * | 9/1991 | Bloomberg et al. | 382/164 |
| 5,181,163 A | 1/1993 | Nakajima et al. | |
| 5,185,809 A * | 2/1993 | Kennedy et al. | 382/131 |
| 5,218,965 A | 6/1993 | Noveck et al. | |
| 5,235,522 A | 8/1993 | Bacus | |
| 5,239,591 A * | 8/1993 | Ranganath | 382/128 |
| 5,263,126 A | 11/1993 | Chang | |
| 5,276,860 A | 1/1994 | Fortier et al. | |
| 5,276,867 A | 1/1994 | Kenley et al. | |
| 5,287,497 A | 2/1994 | Behera | |
| 5,307,287 A | 4/1994 | Cramer, III et al. | |
| 5,340,719 A | 8/1994 | Hajek et al. | |
| 5,355,215 A | 10/1994 | Schroeder et al. | |
| 5,355,445 A | 10/1994 | Shibao et al. | |
| 5,375,606 A | 12/1994 | Slezak et al. | |
| 5,379,366 A | 1/1995 | Noyes | |
| 5,410,250 A * | 4/1995 | Brown | 324/309 |
| 5,418,943 A | 5/1995 | Borgida et al. | |
| 5,418,944 A | 5/1995 | DiPace et al. | |
| 5,434,796 A | 7/1995 | Weininger | |
| 5,435,310 A * | 7/1995 | Sheehan et al. | 600/416 |
| 5,443,791 A | 8/1995 | Cathcart et al. | |
| 5,511,186 A | 4/1996 | Carhart et al. | |
| 5,537,585 A | 7/1996 | Blickenstaff et al. | |
| 5,548,661 A | 8/1996 | Price et al. | |
| 5,554,505 A | 9/1996 | Hajek et al. | |
| 5,615,112 A | 3/1997 | Liu Sheng et al. | |
| 5,657,255 A | 8/1997 | Fink et al. | |
| 5,670,113 A | 9/1997 | Akong et al. | |
| 5,675,819 A | 10/1997 | Schuetze | |
| 5,732,150 A | 3/1998 | Zhou et al. | |
| 5,742,811 A | 4/1998 | Agrawal et al. | |
| 5,751,605 A | 5/1998 | Hurst et al. | |
| 5,806,060 A | 9/1998 | Borgida et al. | |
| 5,808,918 A | 9/1998 | Fink et al. | |
| 5,809,499 A | 9/1998 | Wong et al. | |
| 5,819,266 A | 10/1998 | Agrawal et al. | |
| 5,857,185 A | 1/1999 | Yamaura | |
| 5,862,514 A | 1/1999 | Huse et al. | |
| 5,867,118 A | 2/1999 | McCoy et al. | |
| 5,873,080 A | 2/1999 | Coden et al. | |
| 5,873,083 A | 2/1999 | Jones et al. | |
| 5,892,838 A | 4/1999 | Brady | |
| 5,901,069 A | 5/1999 | Agrafiotis et al. | |
| 5,914,891 A | 6/1999 | McAdams et al. | |
| 5,930,154 A | 7/1999 | Thalhammer-Reyero | |
| 5,940,817 A | 8/1999 | Kishi et al. | |
| 5,950,192 A | 9/1999 | Moore et al. | |
| 5,965,352 A | 10/1999 | Stoughton et al. | |
| 5,966,712 A | 10/1999 | Sabatini et al. | |
| 5,970,482 A | 10/1999 | Pham et al. | |
| 5,970,500 A | 10/1999 | Sabatini et al. | |
| 5,977,890 A | 11/1999 | Rigoutsos | |
| 5,978,804 A | 11/1999 | Dietzman | |
| 5,980,096 A | 11/1999 | Thalhammer-Reyero | |
| 5,989,835 A | 11/1999 | Dunlay et al. | |
| 6,023,659 A | 2/2000 | Seilhamer et al. | |
| 6,035,298 A | 3/2000 | McKearney | |
| 6,073,138 A | 6/2000 | de l'Etraz et al. | |
| 6,081,620 A | 6/2000 | Anderholm | |
| 6,094,652 A | 7/2000 | Faisal | |
| 6,103,479 A | 8/2000 | Taylor | |
| 6,192,165 B1 | 2/2001 | Irons | |
| 6,415,048 B1 * | 7/2002 | Schneider | 382/131 |
| 6,492,810 B1 * | 12/2002 | Hajnal | 324/309 |
| 6,529,705 B1 * | 3/2003 | Keller et al. | 434/362 |

FOREIGN PATENT DOCUMENTS

| | | |
|---|---|---|
| EP | 0 471 650 A1 | 2/1992 |
| EP | 0 811 421 A1 | 6/1997 |
| FR | 2 050 251 | 7/1969 |
| JP | 06-309372 | 4/1994 |
| WO | WO 91/06050 A1 | 10/1990 |
| WO | WO 96/22575 A1 | 1/1996 |
| WO | WP96/25719 | 8/1996 |
| WO | WO 97/42253 A1 | 5/1997 |
| WO | WO 98/15825 | 4/1998 |
| WO | WO 98/38490 | 9/1998 |
| WO | WO 99/05323 | 2/1999 |
| WO | WO 00/15847 | 3/2000 |

OTHER PUBLICATIONS

A.R. Kerlavage et al., *Data Management and Analysis for High-Throughput DNA Sequencing Projects*, IEEE Engineering in Medicine and Biology Magazine, IEEE Inc., New York, vol. 14, No. 6, 1995, pp. 710-717.

C. Allee, *Data Management for Automated Drug Discovery Laboratories*, Laboratory Robotics and Automation, Wiley, vol. 8, No. 5, 1996, pp. 307-310.

Kenneth A. Giuliano et al., *High-Content Screening: A New Approach to Easing Key Bottlenecks in the Drug Discovery Process*, Journal of BioMolecular Screeing, vol. 2, No. 4, 1997, pp. 249-259.

Kenneth A. Giuliano et al., *Fluorescent-protein Biosensors: New Tools for Drug Discovery*, Trends in Biotechnology, vol. 16, 1998, 99. 135-140.

Bruce R. Conway et al., *Quantification of G-Protein Coupled Receptor Internalization Using G-Protein Coupled Receptor-Green Fluorescent Protein Conjugates with the ArrayScan™ High-Content Screening System*, vol. 4, No. 2, 1999, pp. 75-86.

Ethan B. Arutunian et al., *Flexible Software Architecture for User-Interface and Machine Control in Laboratory Automation*, BioTechniques, vol. 25, Oct. 1998, pp. 698-705.

Cellonics, Inc., *Smarter Screening and Lead Optimization with Cellomics High Content Screening Systems and Informatics Tools in an Integrated Drug Discovery Solution*, 1999, 13 pages.

W. Salmonsen et al., *BioJAKE: A Tool for the Creation, Visualization and Manipulation of Metabolic Pathways*, Bioinformatics Centre, 1999, pp. 392-400.

W. Fujibuchi et al., *KEGG and DBGET/LinkDB: Integration of Biological Relationships in Divergent Molecular Biology Data*, Institute for Chemical Research, Kyoto University, 1998, pp. 35-40.

P.D. Karp, *Database Links are a Foundation for Inteoperability*, TibTech, vol. 14, 1996, pp. 273-279.

Paley et al., *Adapting EcoCyc for Use on the World Wide Web*, Gene 172, GC43-GC50, 1996, pp. 43-50.

P.D. Karp, *Computer Corner-Metabolic Databases*, TIBS, 1998, pp. 114-116.

D.L. Taylor et al., *Automated Interactive Microscopy: Measuring and Manipulating the Chemical and Molecular Dynamics of Cells and Tissues*, SPIE, vol. 2678, 1996, pp. 15-27.

D. Lansing Taylor et al., *The New Vision of Light Microscopy, Lasers, Electronic Cameras and Digital Image Analysis with the Most Venerable Instrument of the Life Sciences to Create New Ways of Seeing Living Cells*, American Scientist, vol. 80, 1992, pp. 322-325.

Robert T. Proffitt et al., *A Fluorescence Digital Image Microscopy System for Quantifying Relative Cell Numbers in Tissue Culture Plates*, Cytometry 24, 1996, pp. 204-213.

Overbeek et al., *Representation of Function: The Next Step*, Published on-line Jan. 31, 1997, www.mcs.anl.gov/compbio/publications/function_pap.html, pp. 1-13, printed Feb. 18, 1999.

Karp et al., *Representations of Metabolic Knowledge: Pathways*, Artificial Intelligence Center, ISMB-94, pp. 203-211.

Ogata et al., *KEGG: Kyoto Encyclopedia of Genes and Genomes*, Institute for Chemical Research, Nucleic Acids Research, vol. 27, No. 1, 1999, pp. 29-34.

Heidtke et al., *BioSim - A New Qualitative Simulation Environment for Molecular Biology*, Max-Planck-Institute for Molecular Genetics, ISMB-98, pp. 85-94.

Igarashi et al., *Development of a Cell Signaling Networks Database*, Divisional of Chem-Bio Informations, National Institute of Health Sciences, 1997, pp. 187-197.

Goto et al., *Organizing and Computing Metabolic Pathway Data in Terms of Binary Relations*, Institute for Chemical Research, Kyoto University, 1997, pp. 175-186.

Kraus et al., *Systems Analysis in Cell Biology: From the Phenomenological Description Towards a Computer Model of the Intracellular Signal Transduction Network*, Experientia 49, Birkhauser Verlag, Ch-0410, Basel/Switzerland, 1993, pp. 245-257.

Ogata et al., *Computation with the KEGG Pathway Database*, Institute for Chemical Research, Kyoto University, BioSystems 47, 1998, pp. 119-128.

Karp et al., *EcoCyc: Encyclopedia of Escherichia Coli Genes and Metabolism*, Nucleic Acids Research, vol. 26, No. 1, 1998, pp. 50-53.

Bono et al., *Reconstruction of Amino Acid Biosynthesis Pathways from the Complete Genome Sequence*, Institute for Chemical Research, Kyoto University, by Cold Spring Harbor Laboratory Press, ISSN 1054-9803, 1998, pp. 203-210.

Goto et al., *LIGAND Database for Enzymes, Compounds and Reactions*, Institute for Chemical Research and Graduate School of Agricultural Sciences, Kyoto University, Oxford University Pres, Nucleic Acids Research, vol. 27, No. 1, 1999, pp. 377-379.

Goto et al., *LIGAND: Chemical Database for Enzyme Reactions*, Institute for Chemical Research and Graduate School of Agricultural Sciences, Kyoto University, Oxford University Pres, Bioinformatics, vol. 14, No. 7, 1998, pp. 591-599.

Ermolaeva et al, *Data Management and Analysis for Gene Expression Arrays*, Nature Genetics, vol. 20, Sep. 1998, pp. 19-23.

McGregor et al., *Pharmachphore Fingerprinting, 1. Application to QSAR and Focused Library Design*, Affymax Research Institute, J. Chem. Inf. Computer Science, vol. 39, 1999, pp. 569-574.

Collins et al., *Driving Drug Discovery and Patient Therapy Via the Encapsulation and Fusion of Knowledge*, Momentum Healthcare Ltd., Pharmaceutical Sciences Research Institute, Drug Design and Discovery, vol. 16, 1999, pp. 181-194.

Mark Collins, *Empiricism Strikes Back: Neural Networks in Biotechnology*, Bio/Technology, vol. 11, Feb. 1993, pp. 163-166.

Hopfinger et al., *Extraction of Pharmacophore Information from High-Throughput Screens*, Current Opinion in Biotechnology, vol. 11, 2000, pp. 97-103.

Peter A. Hunt, *QSAR Using 2D Descriptors and TRIPOS' SIMCA*, NRC Terlings Park, Journal of Computer-Aided Molecular Design, vol. 13, 1999, pp. 453-467.

Schmalhofer et al., *Cooperative Knowledge Evolution: A Construction-Integration Approach to Knowledge Discovery in Medicine*, German Research Center for Artificial Intelligence, Methods of Information in Medicine, vol. 37, 1998, pp. 491-500.

Mars et al., *Knowledge Acquistion and Verification Tools for Medical Expert Systems*, Med Decis Making, vol. 7, 1987, pp. 6-11.

Robinson et al., *Self-Organizing Molecular Field Analysis: A Tool for Structure-Activity Studies*, Physical and Theoretical Chemistry Laboratory, Oxford University, J. Med. Chem., vol. 42, 1999, pp. 573-583.

Sung et al., *Evolutionary Optimization in Quantitative Structure-Activity Relationship: An Application of Genetic Neural Networks*, Department of Chemistry, Harvard University, J. Med. Chem., vol. 39, 1996, pp. 1521-1530.

Hans Matter, *Selecting Optimally Diverse Compounds from Structure Databases: A Validation Study of Two-Dimensional and Three-Dimensional Molecular Descriptors*, J. Med. Chem., vol. 40, 1997, pp. 1219-1229.

A. David Rodrigues, *Preclinical Drug Metabolism in the Age of High-Throughput Screening: An Industrial Perspective*, Pharmaceutical Research, vo. 14, No. 11, 1997, pp. 1504-1510.

Gorse et al., *Molecular Diversity and Its Analysis*, DDT, vol. 4, No. 6, Jun. 1999, pp. 257-264.

Cramer et al., *Prospective Identification of Biologically Active Structures by Topomer Shape Similarity Searching*, Tripos, Inc. and Bristol-Meyers Squibb, J. Med. Chem., vol. 42, 1999, pp. 3919-3933.

Manallack et al., *Neural Networks in Drug Discovery: Have They Lived Up to Their Promise?*, Eur. J. Med. Chem., vo. 43, 1999, pp. 195-208.

*The Knowledge Access Suite - Much More Then Just Data Mining*, www.datamining.com/ka-suite.htm (various other articles attached all accessed at dataming.com), printed Apr. 6, 2000.

*Data Mining: An Introduction: Clementine-Working With Health Care*, www.spss.com/cool/papers/clem_healthcare1.htm (other various downloads from this site) printed Apr. 9, 2000.

*Cognos Scenario*, www.cognos.com/scenario/index.html, printed Apr. 9, 2000.

*Discover News Drugs*, Discover Synt:em, www.syntem.com, printed Apr. 9, 2000.

*DIVA Desktop Decision Support for Life Science Research for Windows 95, Windows 98, Windows NT*, Oxford Molecular 1999, pp. 1-4.

*Oxford Molecular - Solutions for Discovery Research*, www.oxmol.com/software/diamond/background.shtml (various other articles from this site), printed Apr. 9, 2000.

MDL Information Systems, Inc., www.mdli.com/cgi/dynamic/product.html?uid=$uid&key=$key&id=40 (various other articles from this site), printed Apr. 9, 2000.

Tripos, Inc. Discovery Research, www.tripos.com/resarch/typapp.html various other articles from this site), printed Apr. 9, 2000.

*Bionumerik Pharmaceuticals*, Red Herring Magazine, www.rhventure.com/mag/issue67/news-feature-du99-bionum.html, pp. 1-2, printed Apr. 9, 2000.

*Chemistry and Biological Sciences*, Silicon Graphics, Inc. (SGI), 2000, www.sgi.com/chembio/cust_success/bionumerik.html, pp. 1-2. printed Apr. 9, 2000.

*CS 267 Assignment One - Drug Design*garnet.berkeley.edu/~abeand/cs267/assignment1.html, pp. 1-2, printed Apr. 9, 2000.

*Cray and BioNumerik Pharmaceuticals: Engineering More Rapid Cures for Today's Diseases*, www.cray.com/features/bionumerik.html, pp. 1-3, printed Apr. 9, 2000.

*BioNumerik Reports Preclinical Antitumor Data on Two Novel Supercomputer Engineered Anticancer Agents at 89th Annual AACR Conference*www.prostatecancer.com/otherinfo/story2-aacs.html-ssi, pp. 1-3, printed Apr. 9, 2000.

*Agile Business Rule Processing*, The Haley Enterprise, Inc., 1999, pp. 1-9.

*Knowledge Management and Knowledge Automation Systems*, Gallagher Financial Systems, Inc., pp. 1-6, printed Apr. 9, 2000.

Various pages from www.haley.com/4013219860515857/0000025120WhitePapers.html, etc., printed Apr. 9, 2000.

Arbour Group, *Software Specialist to the Pharmaceutical and Medical Device Industries*, www.arbourgroup.com (various other articles from this site) printed Apr. 9, 2000.

*Nanodesign - Partners in Drug Discover*, EMD Facts-Evolutionary Molecular Design, www.nanodesign.com/EMD_facts.htm (various other articles from this site) printed Apr. 9, 2000.

*BIOREASON-Automated Reasoning Systems for Drug Discovery*, www.bioreason.com(various other articles from this site) printed Apr. 9, 2000.

*Next Generation Software Tools for Early Drug Development*, www.innaphase.com/pub/products.htm (various other articles from this site) printed Apr. 9, 2000.

*LION Bioscience - Genomics, Informatics, Solutions*, www.lion-ag.de (various other articles from this site) printed Apr. 9, 2000.

*Inpharmatica - World-Class* Bioinformatics, www.inpharmatica.co.uk (various other articles from this site) printed Apr. 9, 2000.

*Printed Explorer: Enabling Knowledge - Led R&D Projects*, Synomics, www.synomics.com/m/products/projectexplorer.htm, pp. 1-3 printed Apr. 9, 2000.

*PharMatrix - Providing Information, Knowledge & Project Management Solutions for Pharmaceutical Discovery & Development*, www.base4.com (various other articles from this site) printed Apr. 9, 2000.

Rowe et al., *Artificial Intelligence in Pharmaceutical Product Formulation: Neural Computing and Emerging Technologies*, PSTT, vol. 1, No. 5, Aug. 1998, pp. 200-205.

Rowe et al., *Artificial Intelligence in Pharmaceutical Product Formulation: Knowledge-Based and Expert* Systems, PSTT, vol. 1, No. 4, Jul. 1998, pp. 153-139.

Wayne C. Guida, *Software for Structure-Based Drug Design*, Current Opinion in Structural Biology, vol. 4, 1994, pp. 777-781.

*Bioinformatics, Pharmaceutical Informatics and Drug Discovery*, www.basefour.com/what_is.html, pp. 1-3, printed Apr. 9, 2000.

*Commercial Bioinformatics Software*, www.uk.embnet.org/data/www/CCP11/commercial_software.txt.html, pp. 1-12, printed Apr. 9, 2000.

Hwa A. Lim, *Bioinformatics and Cheminformatics in the Drug Discovery Cycle*, in: Lecture Notes in Computer Science#1278, 1997, pp. 30-43.

Nathan Goodman, *The Fundamental Principles for Constructing A Successful Biological Laboratory Informatics System*, pp. 1-11.

Rebecca N. Lawrence, *Enhancing Information Sharing*, DDT, vol. 4, No. 11, Nov. 1999, pp. 494-495.

Matthew Thorne, *InfoTech Pharma '98: Managing The Knowledge*, DDT, vol. 3, No. 5, May 1998, pp. 197-199.

Quinn et al., *Development of Internet-Based Multimedia Applications*, TiBs 24, Aug. 1999, pp. 1-4.

Watt et al., *Approaches to Higher-Throughput Pharmacokinetics (HTPK) in Drug Discovery*, DDT, vol. 5, No. 1, Jan. 2000, pp. 17-24.

Craw et al., *Automated Knowledge Refinement for Rule-Based Formulation Expert System*, PSTT, vol. 2, No. 9, Sep. 1999, pp. 383-385.

Steve Bottomley, *Bioinformatics - Value-added Databases*, DDT, vol. 4, No. 1, Jan. 1999, pp. 42-44; DDT, vol. 4, No. 10, Oct. 1999, pp. 482-484.

Andrade et al., *Bioinformatics: From Genome Data to Biological Knowledge*, Current Opinion in Biotechnology, vol. 8, 1997, pp. 675-683.

Profiles Monitor, various articles, DDT, vol. 3, No. 11, Nov. 1998, pp. 525-527.

Monitor, various articles, DDT, vol. 3, No. 9, Sep. 1998, pp. 426-428.

Peter Murray-Rust, *Bioinformatics and Drug Discovery*, Current Opinion in Biotechnology, vol. 5, 1994, pp. 648-653.

Blaschke et al., *Automatic Extraction of Biological Information from Scientific Text: Protein-Protein Interactions*, Protein Design Group, ISBM-99, pp. 60-67.

Chen et al., *Automatic Construction of Networks of Concepts Characterizing Document Databases*, IEEE Transactions on Systems, Man, and Cybermetics, vol. 22, No. 5, Sep./Oct. 1992, pp. 885-902.

Chen et al., *An Algorithmic Approach to Concept Exploration in a Large Knowledge Network (Automatic Thesaurus Consultation): Symbolic Branch-and-Bound Search vs. Connectionist Hopfield Net Activation*, Journal of the American Society for Information Science, vol. 46, No. 5, 1995, pp. 348-369.

Craven et al., *Constructing Biological Bases by Extracting Information from Text Sources*, American Association for Artificial Intelligence, ISMB-99, pp. 77-86.

Gordon et al., *Toward Discovery Support Systems: A Replication, Re-Examination, and Extension of Swanson's Work on Literature-Based Discovery of a Connection Between Raynaud's and Fish Oil*, Journal of the American Society for Information Science, vol. 47, No. 2, 1996, pp. 116-128.

Swanson et al., *An Interactive System for Finding Complementary Literatures: A Stimulus to Scientific Discovery*, www.kiwi.uchicago.edu/webwork/alabtext.html (other various downloads from this site) printed from this site May 23, 2000.

Peter D. Karp, *Pathway Databases: A Case Study in Computational Symbolic Theories*, Computers and Science, vol. 293, Sep. 14, 2001, pp. 2040-2044.

David K. Gifford, *Blazing Pathways Through Genetic Mountains*, Computers and Science, vol. 293, Sep. 14, 2001, pp. 2049-2051.

\* cited by examiner

ARRAY SCAN MODULE

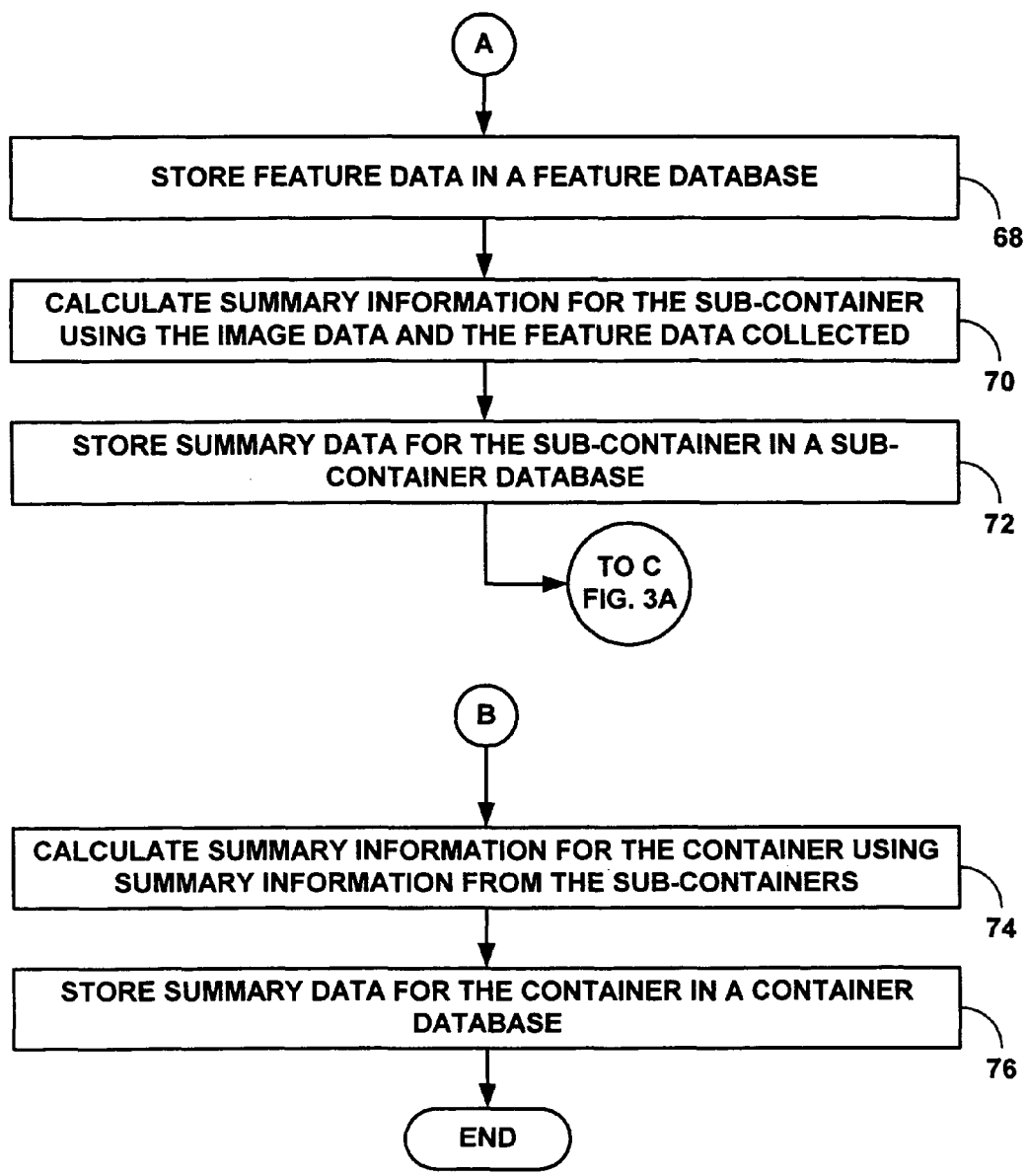

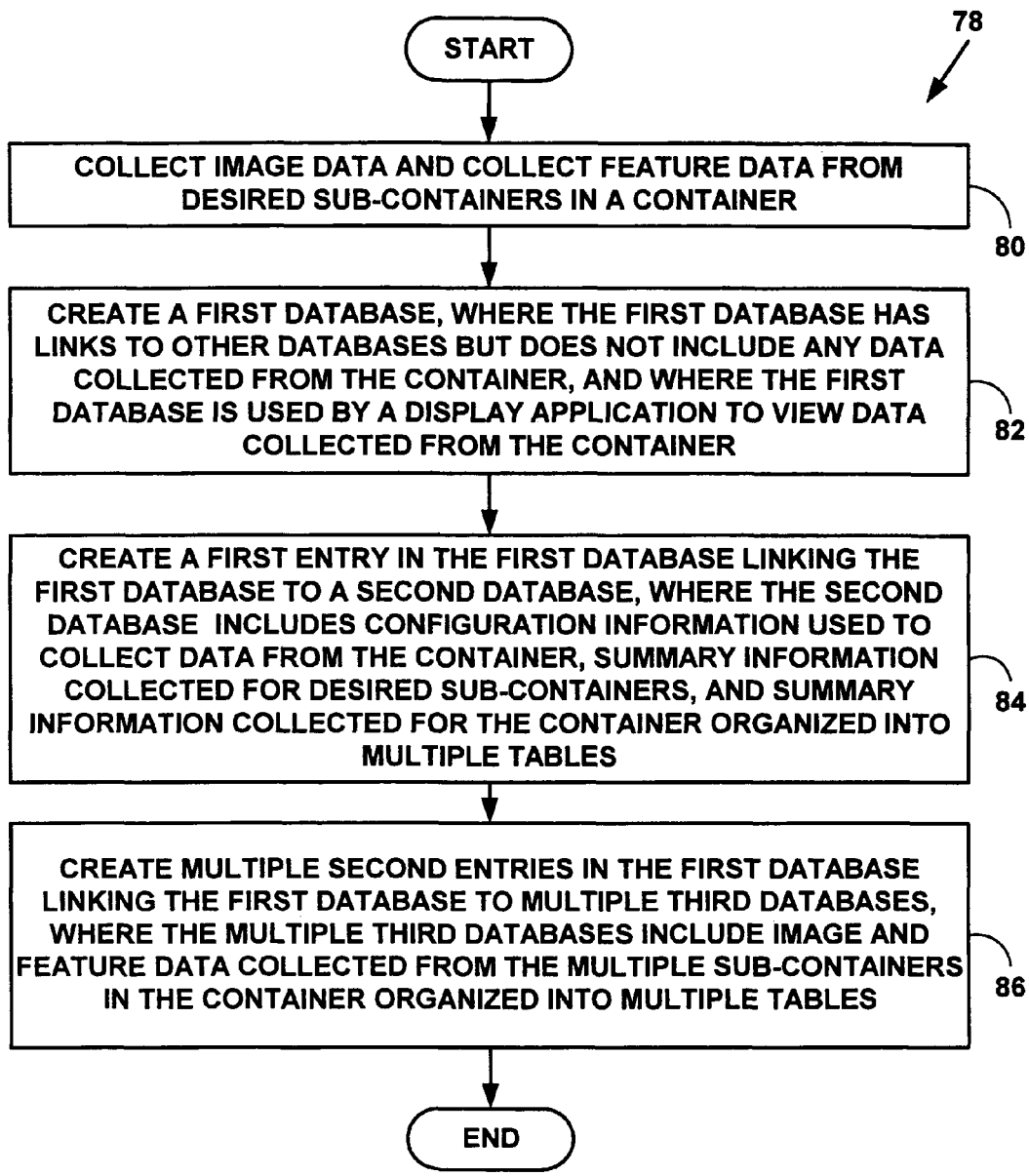

SYSTEM DATABASE 92
TABLES

METHOD AND SYSTEM FOR EFFICIENT COLLECTION AND STORAGE OF EXPERIMENTAL DATA

CROSS REFERENCES TO RELATED APPLICATIONS

This applications claims priority from U.S. Provisional Applications No. 60/108,291, filed on Nov. 13, 1998, 60/110,643, filed on Dec. 1, 1998, 60/140,240, filed on Jun. 21, 1999, 60/142,375, filed on Jul. 6, 1999, and 60/142,646 filed on Jul. 6, 1999.

FIELD OF THE INVENTION

This invention relates to collecting and storing experimental data. More specifically, it relates to methods and system for efficient collection and storage of experimental data from automated feature-rich, high-throughput experimental data collection systems.

BACKGROUND OF THE INVENTION

Historically, the discovery and development of new drugs has been an expensive, time consuming and inefficient process. With estimated costs of bringing a single drug to market requiring an investment of approximately 8 to 12 years and approximately $350 to $500 million, the pharmaceutical research and development market is in need of new technologies that can streamline the drug discovery process. Companies in the pharmaceutical research and development market are under fierce pressure to shorten research and development cycles for developing new drugs, while at the same time, novel drug discovery screening instrumentation technologies are being deployed, producing a huge amount of experimental data.

Innovations in automated screening systems for biological and other research are capable of generating enormous amounts of data. The massive volumes of feature-rich data being generated by these systems and the effective management and use of information from the data has created a number of very challenging problems. As is known in the art, "feature-rich" data includes data wherein one or more individual features of an object of interest (e.g., a cell) can be collected. To fully exploit the potential of data from high-volume data generating screening instrumentation, there is a need for new informatic and bioinformatic tools.

Identification, selection, validation and screening of new drug compounds is often completed at a nucleotide level using sequences of Deoxyribonucleic Acid ("DNA"), Ribonucleic Acid ("RNA") or other nucleotides. "Genes" are regions of DNA, and "proteins" are the products of genes. The existence and concentration of protein molecules typically help determine if a gene is "expressed" or "repressed" in a given situation. Responses of genes to natural and artificial compounds are typically used to improve existing drugs, and develop new drugs. However, it is often more appropriate to determine the effect of a new compound on a cellular level instead of a nucleotide level.

Cells are the basic units of life and integrate information from DNA, RNA, proteins, metabolites, ions and other cellular components. New compounds that may look promising at a nucleotide level may be toxic at a cellular level. Florescence-based reagents can be applied to cells to determine ion concentrations, membrane potentials, enzyme activities, gene expression, as well as the presence of metabolites, proteins, lipids, carbohydrates, and other cellular components.

There are two types of cell screening methods that are typically used: (1) fixed cell screening; and (2) live cell screening. For fixed cell screening, initially living cells are treated with experimental compounds being tested. No environmental control of the cells is provided after application of a desired compound and the cells may die during screening. Live cell screening requires environmental control of the cells (e.g., temperature, humidity, gases, etc.) after application of a desired compound, and the cells are kept alive during screening. Fixed cell assays allow spatial measurements to be obtained, but only at one point in time. Live cell assays allow both spatial and temporal measurements to be obtained.

The spatial and temporal frequency of chemical and molecular information present within cells makes it possible to extract feature-rich cell information from populations of cells. For example, multiple molecular and biochemical interactions, cell kinetics, changes in sub-cellular distributions, changes in cellular morphology, changes in individual cell subtypes in mixed populations, changes and sub-cellular molecular activity, changes in cell communication, and other types of cell information can be obtained.

The types of biochemical and molecular cell-based assays now accessible through fluorescence-based reagents is expanding rapidly. The need for automatically extracting additional information from a growing list of cell-based assays has allowed automated platforms for feature-rich assay screening of cells to be developed. For example, the ArrayScan System by Cellomics, Inc. of Pittsburgh, Pa., is one such feature-rich cell screening system. Cell based systems such as FLIPR, by Molecular Devices, Inc. of Sunnyvale, Calif., FMAT, of PE Biosystems of Foster City, Calif., ViewLux by EG&G Wallac, now a subsidiary of Perkin-Elmer Life Sciences of Gaithersburg, Md., and others also generate large amounts of data and photographic images that would benefit from efficient data management solutions. Photographic images are typically collected using a digital camera. A single photographic image may take up as much as 512 Kilobytes ("KB") or more of storage space as is explained below. Collecting and storing a large number of photographic images adds to the data problems encountered when using high throughput systems. For more information on fluorescence based systems, see "Bright ideas for high-throughput screening—One-step fluorescence HTS assays are getting faster, cheaper, smaller and more sensitive," by Randy Wedin, Modern Drug Discovery, Vol. 2(3), pp. 61-71, May/June 1999.

Such automated feature-rich cell screening systems and other systems known in the art typically include microplate scanning hardware, fluorescence excitation of cells, fluorescence captive emission optics, a photographic microscopic with a camera, data collection, data storage and data display capabilities. For more information on feature-rich cell screening see "High content fluorescence-based screening," by Kenneth A. Guiliano, et al., Journal of Biomolecular Screening, Vol. 2, No. 4, pp. 249-259, Winter 1997, ISSN 1087-0571, "PTH receptor internalization," Bruce R. Conway, et al., Journal of Biomolecular Screening, Vol. 4, No. 2, pp. 75-68, April 1999, ISSN 1087-0571, "Fluorescent-protein biosensors: new tools for drug discovery," Kenneth A. Giuliano and D. Lansing Taylor, Trends in Biotechnology, ("TIBTECH"), Vol. 16, No. 3, pp. 99-146, March 1998, ISSN 0167-7799, all of which are incorporated by reference.

An automated feature-rich cell screening system typically automatically scans a microplate plate with multiple wells and acquires multi-color fluorescence data of cells at one or more instances of time at a pre-determined spatial resolution. Automated feature-rich cell screen systems typically support multiple channels of fluorescence to collect multi-color fluorescence data at different wavelengths and may also provide the ability to collect cell feature information on a cell-by-cell basis including such features as the size and shape of cells and sub-cellar measurements of organelles within a cell.

The collection of data from high throughput screening systems typically produces a very large quantity of data and presents a number of bioinformatics problems. As is known in the art, "bioinformatic" techniques are used to address problems related to the collection, processing, storage, retrieval and analysis of biological information including cellular information. Bioinformatics is defined as the systematic development and application of information technologies and data processing techniques for collecting, analyzing and displaying data obtained by experiments, modeling, database searching, and instrumentation to make observations about biological processes. The need for efficient data management is not limited to feature-rich cell screening systems or to cell based arrays. Virtually any instrument that runs High Throughput Screening ("HTS") assays also generate large amounts of data. For example, with the growing use of other data collection techniques such as DNA arrays, bio-chips, microscopy, micro-arrays, gel analysis, the amount of data collected, including photographic image data is also growing exponentially. As is known in the art, a "bio-chip" is a stratum with hundreds or thousands of absorbent micro-gels fixed to its surface. A single bio-chip may contain 10,000 or more micro-gels. When performing an assay test, each micro-gel on a bio-chip is like a micro-test tube or a well in a microplate. A bio-chip provides a medium for analyzing known and unknown biological (e.g., nucleotides, cells, etc.) samples in an automated, high-throughput screening system.

Although a wide variety of data collection techniques can be used, cell-based high throughput screening systems are used as an example to illustrate some of the associated data management problems encountered by virtually all high throughput screening systems. One problem with collecting feature-rich cell data is that a microplate plate used for feature-rich screening typically includes 96 to 1536 individual wells. As is known in the art, a "microplate" is a flat, shallow dish that stores multiple samples for analysis. A "well" is a small area in a microplate used to contain an individual sample for analysis. Each well may be divided into multiple fields. A "field" is a sub-region of a well that represents a field of vision (i.e., a zoom level) for a photographic microscope. Each well is typically divided into one to sixteen fields. Each field typically will have between one and six photographic images taken of it, each using a different light filter to capture a different wavelength of light for a different fluorescence response for desired cell components. In each field, a predetermined number of cells are selected to analyze. The number of cells will vary (e.g., between ten and one hundred). For each cell, multiple cell features are collected. The cell features may include features such as size, shape, etc. of a cell. Thus, a very large amount of data is typically collected for just one well on a single microplate.

From a data volume perspective, the data to be saved for a well can be estimated by number of cell feature records collected and the number of images collected. The number of images collected can be typically estimated by: (number of wells×number of fields×images per field). The current size of an image file is approximately 512 Kilobytes ("KB") of uncompressed data. As is known in the art, a byte is 8-bits of data. The number of cell feature records can typically be estimated by: (number of wells×number of fields×cells per field×features per cell). Data collected from multiple wells on a microplate is typically formatted and stored on a computer system. The collected data is stored in format that can be used for visual presentation software, and allow for data mining and archiving using bioinformatic techniques.

For example, in a typical scenario, scanning one low density microplate with 96 wells, using four fields per well, three images per field and an image size of 512 Kbytes per image, generates about 1,152 images and about 576 megabytes ("MB") of image data (i.e., (96×4×3×512×(1 KB=1024 bytes)/(1 MB=(1024 bytes×1024 bytes))=576 MB). As is known in the art, a megabyte is $2^{20}$ or 1,048,576 bytes and is commonly interpreted as "one million bytes."

If one hundred cells per field are selected with ten features per cell calculated, such a scan also generates (96×4×100×10)=288,000 cell feature records, whose data size varies with the amount of cell features collected. This results in about 12,000 MB of data being generated per day and about 60,000 MB per week, scanning the 96 well microplates twenty hours a day, five days a week.

In a high data volume scenario based on a current generation of feature-rich cell screening systems, scanning one high-density microplate with 384 wells, using sixteen fields per well, four images per field, 100 cells per field, ten features per cell, and 512 KB per image, generates about 24,576 images or about 12,288 MB of image data and about 6,144,000 cell feature records. This results in about 14,400 MB of data being generated per day and about 100,800 MB per week, scanning the 384 well microplates twenty-four hours a day, seven days a week.

Since multiple microplates can be scanned in parallel, and multiple automated feature-rich cell screening systems can operate 24 hours a day, seven days a week, and 365 days a year, the experimental data collected may easily exceed physical storage limits for a typical computer network. For example, disk storage on a typical computer network may be in the range from about ten gigabytes ("GB") to about one-hundred GB of data storage. As is known in the art, a gigabyte is $2^{30}$ bytes, or 1024 MB and is commonly interpreted as "one billion bytes."

The data storage requirements for using automated feature-rich cell screening on a conventional computer network used on a continuous basis could easily exceed a terabyte ("TB") of storage space, which is extremely expensive based on current data storage technologies. As is known in the art, one terabyte equals $2^{40}$ bytes, and is commonly interpreted as "one trillion bytes." Thus, collecting and storing data from an automated feature-rich cell screening system may severely impact the operation and storage of a conventional computer network.

Another problem with feature-rich cell screening systems is even though a massive amount of cell data is collected, only a very small percentage of the total cell feature data and image data collected will ever be used for direct visual display. Nevertheless, to gather statistically relevant information about a new compound all of the cell data generated, is typically stored on a local hard disk and available for analysis. This may also severely impact a local hard disk storage.

Yet another problem is that microplate scan results information for one microplate can easily exceed about 1,000 database records per plate, and cell feature data and image data can easily exceed about 6,000,000 database records per plate. Most conventional databases used on personal computers can not easily store and manipulate such a large number of data records. In addition, waiting relatively long periods of time to open such a large database on a conventional computer personal computer to query and/or display data may severely affect the performance of a network and may quickly lead to user frustration or user dissatisfaction.

Thus, it is desirable to provide a data storage system that can be used for feature-rich screening on a continuous basis. The data storage system should provide a flexible and scalable repository of cell data that can be easily managed and allows data to be analyzed, manipulated and archived.

SUMMARY OF THE INVENTION

In accordance with preferred embodiments of the present invention, some of the problems associated with collecting and storing feature-rich experimental data are overcome. Methods and system for efficient collection and storage of experimental data is provided.

One aspect of the present invention includes a method for collecting experimental data. The method includes collecting image and feature data from desired sub-containers within a container. The image and feature data is stored in multiple image and feature databases. Summary data calculated for the desired sub-containers and the container are stored in sub-container and container databases.

Another aspect of the present invention includes a method for storing experimental data on a computer system. The method includes collecting image data and feature data from desired sub-containers in a container. The image and feature data is stored in multiple third databases comprising multiple database tables. Summary data calculated for desired sub-containers and the container is stored in a second database comprising multiple database tables. A first database is created that is a "pass-through" database. The first database includes a pass-through database table with links to the second database and links to the multiple third databases, but does not include any data collected from the container.

Another aspect of the present invention includes a method for spooling experimental data off devices that collect the data to a number of different remote storage locations. Links in a pass-through database table in a first database are updated to reflect the new locations of second database and multiple third databases.

Another aspect of the present invention includes a method for hierarchical management of experimental data. A pre-determined storage removal policy is applied to database files in a database. If any database files match the pre-determined storage removal policy, the database files are copied into a layer in a multi-layered hierarchical storage management system. The original database files are replaced with placeholder files that include a link to the original database files in the layer in the hierarchical storage management system.

Another aspect of the invention includes presenting the experimental data from a display application on a computer. The data presented by the display application is obtained from multiple databases obtained from multiple locations remote to the computer. The data displayed appears to be obtained from databases on local storage on the computer instead of from the remote locations.

Another aspect of the invention includes a data storage system that provides virtually unlimited amounts of "virtual" disk space for data storage at multiple local and remote storage locations for storing experimental data that is collected.

These methods and system may allow experimental data from high-throughput data collection systems to be efficiently collected, stored, managed and displayed. For example, the methods and system can be used for, but is not limited to, storing managing and displaying cell image data and cell feature data collected from microplates including multiple wells or bio-chips including multiple micro-gels in which an experimental compound has been applied to a population of cells.

The methods and system may provide a flexible and scalable repository of experimental data that can be easily managed and allows the data to be analyzed, manipulated and archived. The methods and system may improve the identification, selection, validation and screening of new experimental compounds (e.g., drug compounds). The methods and system may also be used to provide new bioinformatic techniques used to make observations about experimental data.

The foregoing and other features and advantages of preferred embodiments of the present invention will be more readily apparent from the following detailed description. The detailed description proceeds with references to the accompanying drawings.

BRIEF DESCRIPTION OF THE DRAWINGS

Preferred embodiments of the present invention are described with reference to the following drawings, wherein:

FIGS. 3A and 3B are a flow diagram illustrating a method for collecting experimental data;

FIG. 4 is a flow diagram illustrating a method for storing experimental data;

DETAILED DESCRIPTION OF PREFERRED EMBODIMENTS

Exemplary Data Storage System

Figure 1A:
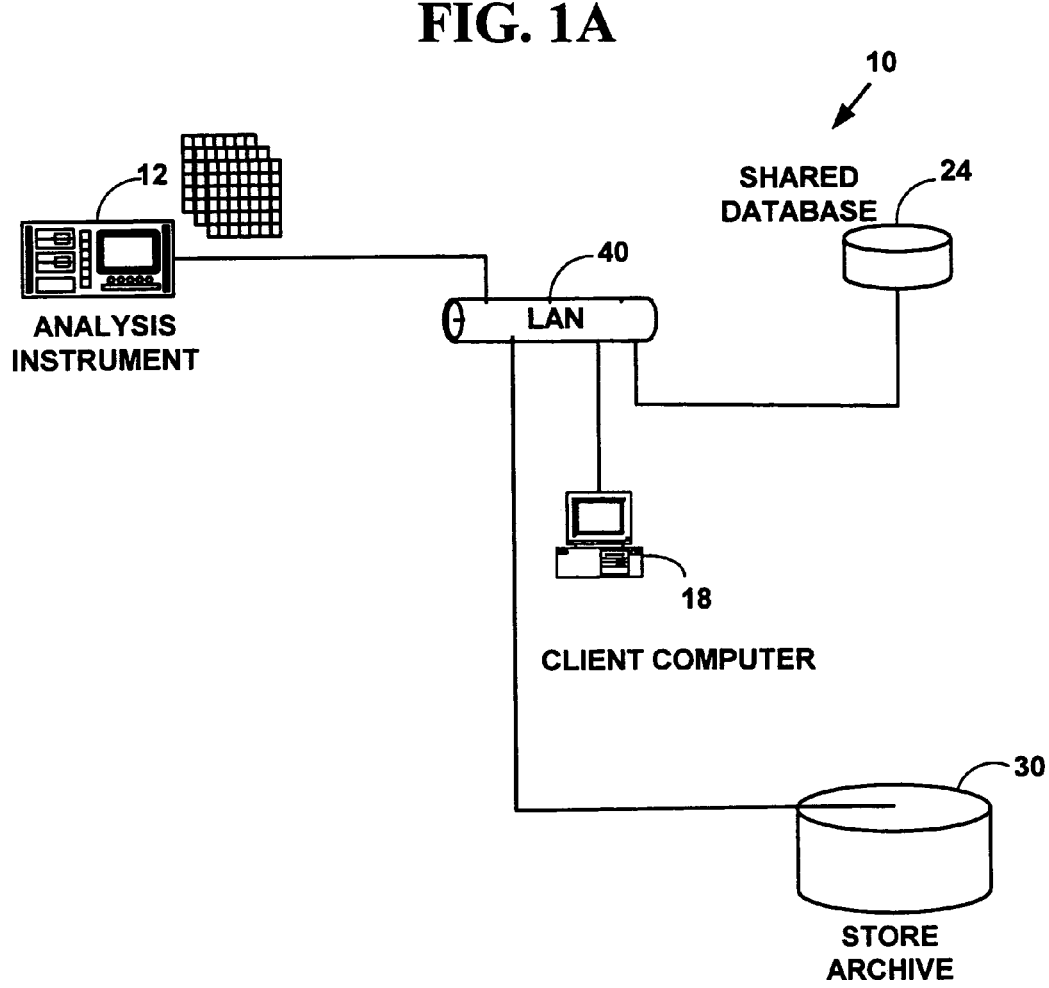
FIG. 1A is a block diagram illustrating an exemplary experimental data storage system.

FIG. 1A illustrates an exemplary data storage system 10 for preferred embodiments of the present invention. The exemplary data storage system 10 includes an analysis instrument 12, connected to a client computer 18, a shared database 24 and a data store archive 30 with a computer network 40. The analysis instrument 12 includes any scanning instrument capable of collecting feature-rich experimental data, such as nucleotide, cell or other experimental data, or any analysis instrument capable of analyzing feature-rich experimental data. As is known in the art, "feature-rich" data includes data wherein one or more individual features of an object of interest (e.g., a cell) can be collected. The client computer 18 is any conventional computer including a display application that is used to lead a scientist or lab technician through data analysis. The shared database 24 is a multi-user, multi-view relational database that stores data from the analysis instrument 12. The data archive 30 is used to provide virtually unlimited amounts of "virtual" disk space with a multi-layer hierarchical storage management system. The computer network 40 is any fast Local Area Network ("LAN") (e.g., capable of data rates of 100 Mega-bit per second or faster). However, the present invention is not limited to this embodiment and more or fewer, and equivalent types of components can also be used. Data storage system 10 can be used for virtually any system capable of collecting and/or analyzing feature-rich experimental data from biological and non-biological experiments.

Figure 1B:
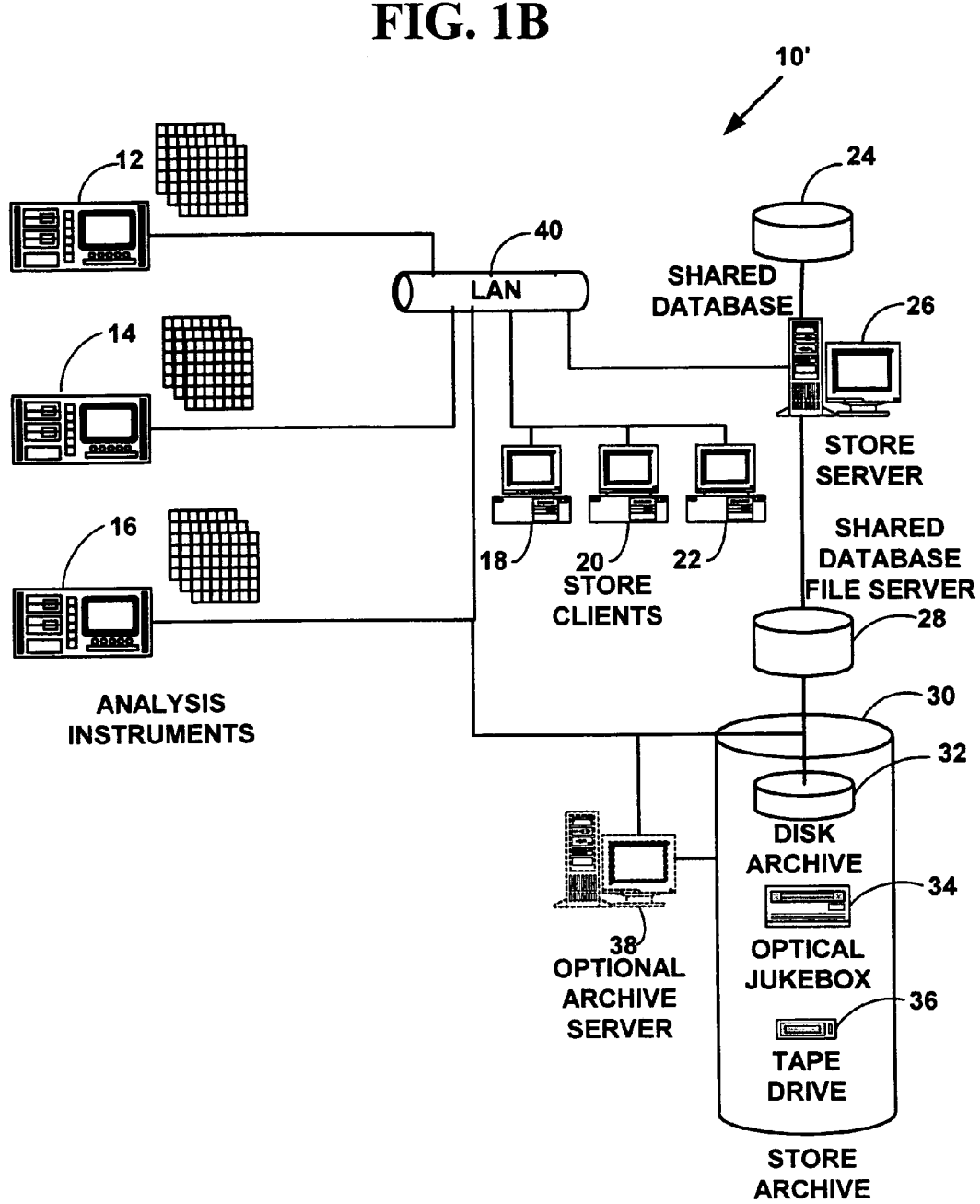
FIG. 1B is a block diagram illustrating an exemplary experimental data storage system.

FIG. 1B illustrates an exemplary data storage system 10' for one preferred embodiment of the present invention with specific components. However, the present invention is not limited to this one preferred embodiment, and more or fewer, and equivalent types of components can also be used. The data storage system 10' includes one or more analysis instruments 12, 14, 16, for collecting and/or analyzing feature-rich experimental data, one or more data store client computers, 18, 20, 22, a shared database 24, a data store server 26, and a shared database file server 28. A data store archive 30 includes any of a disk archive 32, an optical jukebox 34 or a tape drive 36. The data store archive 30 can be used to provide virtually unlimited amounts of "virtual" disk space with a multi-layer hierarchical storage management system without changing the design of any databases used to stored collected experimental data as is explained below. The data store archive 30 can be managed by an optional data archive server 38. Data storage system 10' components are connected by a computer network 40. However, more or fewer data store components can also be used and the present invention is not limited to the data storage system 10' components illustrated in FIG. 1B.

In one exemplary preferred embodiment of the present invention, data storage system 10' includes the following specific components. However, the present invention is not limited to these specific components and other similar or equivalent components may also be used. Analysis instruments 12, 14, 16, comprise a feature-rich array scanning system capable of collecting and/or analyzing experimental data such as cell experimental data from microplates, DNA arrays or other chip-based or bio-chip based arrays. Bio-chips include any of those provided by Motorola Corporation of Schaumburg, Ill., Packard Instrument, a subsidiary of Packard BioScience Co. of Meriden, Conn., Genometrix, Inc. of Woodlands, Tex., and others.

Analysis instruments 12, 14, 16 include any of those provided by Cellomics, Inc. of Pittsburgh, Pa., Aurora Biosciences Corporation of San Diego, Calif., Molecular Devices, Inc. of Sunnyvale, Calif., PE Biosystems of Foster City, Calif., Perkin-Elmer Life Sciences of Gaithersburg, Md., and others. The one or more data store client computers, 18, 20, 22, are conventional personal computers that include a display application that provides a Graphical User Interface ("GUI") to a local hard disk, the shared database 24, the data store server 26 and/or the data store archive 30. The GUI display application is used to lead a scientist or lab technician through standard analyses, and supports custom and query viewing capabilities. The display application GUI also supports data exported into standard desktop tools such as spreadsheets, graphics packages, and word processors.

The data store client computers 18, 20, 22 connect to the store server 26 through an Open Data Base Connectivity ("ODBC") connection over network 40. In one embodiment of the present invention, computer network 40 is a 100 Mega-bit ("Mbit") per second or faster Ethernet, Local Area Network ("LAN"). However, other types of LANs could also be used (e.g., optical or coaxial cable networks). In addition, the present invention is not limited to these specific components and other similar components may also be used.

As is known in the art, OBDC is an interface providing a common language for applications to gain access to databases on a computer network. The store server 26 controls the storage based functions plus an underlying Database Management System ("DBMS").

The shared database 24 is a multi-user, multi-view relational database that stores summary data from the one or more analysis instruments 12, 14, 16. The shared database 24 uses standard relational database tools and structures. The data store archive 30 is a library of image and feature database files. The data store archive 30 uses Hierarchical Storage Management ("HSM") techniques to automatically manage disk space of analysis instruments 12, 14, 16 and the provide a multi-layer hierarchical storage management system. The HSM techniques are explained below.

An operating environment for components of the data storage system 10 and 10' for preferred embodiments of the present invention include a processing system with one or more high-speed Central Processing Unit(s) ("CPU") and a memory. In accordance with the practices of persons skilled in the art of computer programming, the present invention is described below with reference to acts and symbolic representations of operations or instructions that are performed by the processing system, unless indicated otherwise. Such acts and operations or instructions are referred to as being "computer-executed" or "CPU executed."

It will be appreciated that acts and symbolically represented operations or instructions include the manipulation of electrical signals by the CPU. An electrical system represents data bits which cause a resulting transformation or reduction of the electrical signals, and the maintenance of data bits at memory locations in a memory system to thereby reconfigure or otherwise alter the CPU's operation, as well as other processing of signals. The memory locations where data bits are maintained are physical locations that have particular electrical, magnetic, optical, or organic properties corresponding to the data bits.

The data bits may also be maintained on a computer readable medium including magnetic disks, optical disks, organic memory, and any other volatile (e.g., Random Access Memory ("RAM")) or non-volatile (e.g., Read-Only Memory ("ROM")) mass storage system readable by the CPU. The computer readable medium includes cooperating or interconnected computer readable medium, which exist exclusively on the processing system or be distributed among multiple interconnected processing systems that may be local or remote to the processing system.

Array Scan Module Architecture

Figure 2:
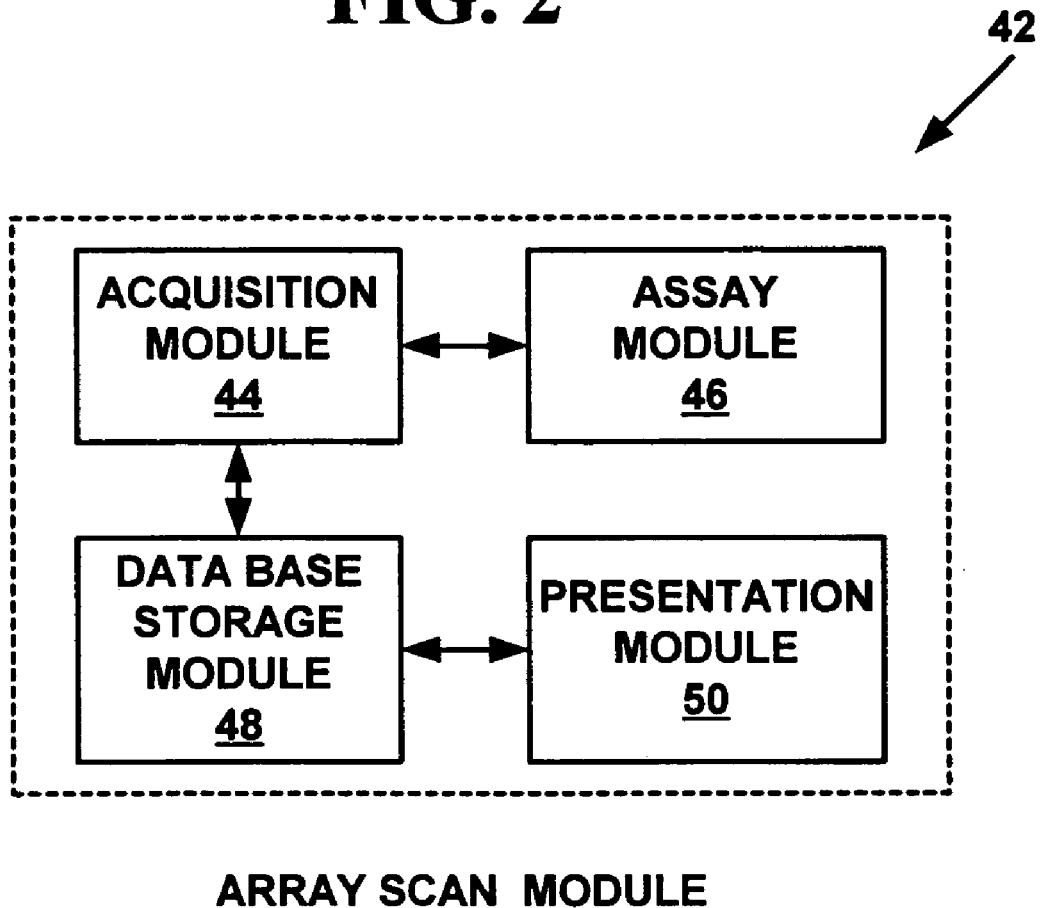
FIG. 2 is a block diagram illustrating an exemplary array scan module architecture.

FIG. 2 is a block diagram illustrating an exemplary array scan module 42 architecture. The array scan module 42, such as one associated with analysis instrument 12, 14, 16 (FIG. 1B) includes software/hardware that is divided into four functional groups or modules. However, more of fewer functional modules can also be used and the present invention is not limited to four functional modules. The Acquisition Module 44 controls a robotic microscope and digital camera, acquires images and sends the images to the Assay Module 46. The Assay Module 46 "reads" the images, creates graphic overlays, interprets the images collects feature data and returns the new images and feature data extracted from the images back to the Acquisition Module 44. The Acquisition Module 44 passes the image and interpreted feature data to the Data Base Storage Module 48. The Data Base Storage Module 48 saves the image and feature information in a combination of image files and relational database records. The store clients 18, 20, 22 use the Data Base Storage Module 48 to access feature data and images for presentation and data analysis by the Presentation Module 50. The Presentation Module 50 includes a display application with a GUI as was discussed above.

Collection of Experimental Data

Figure 3A:
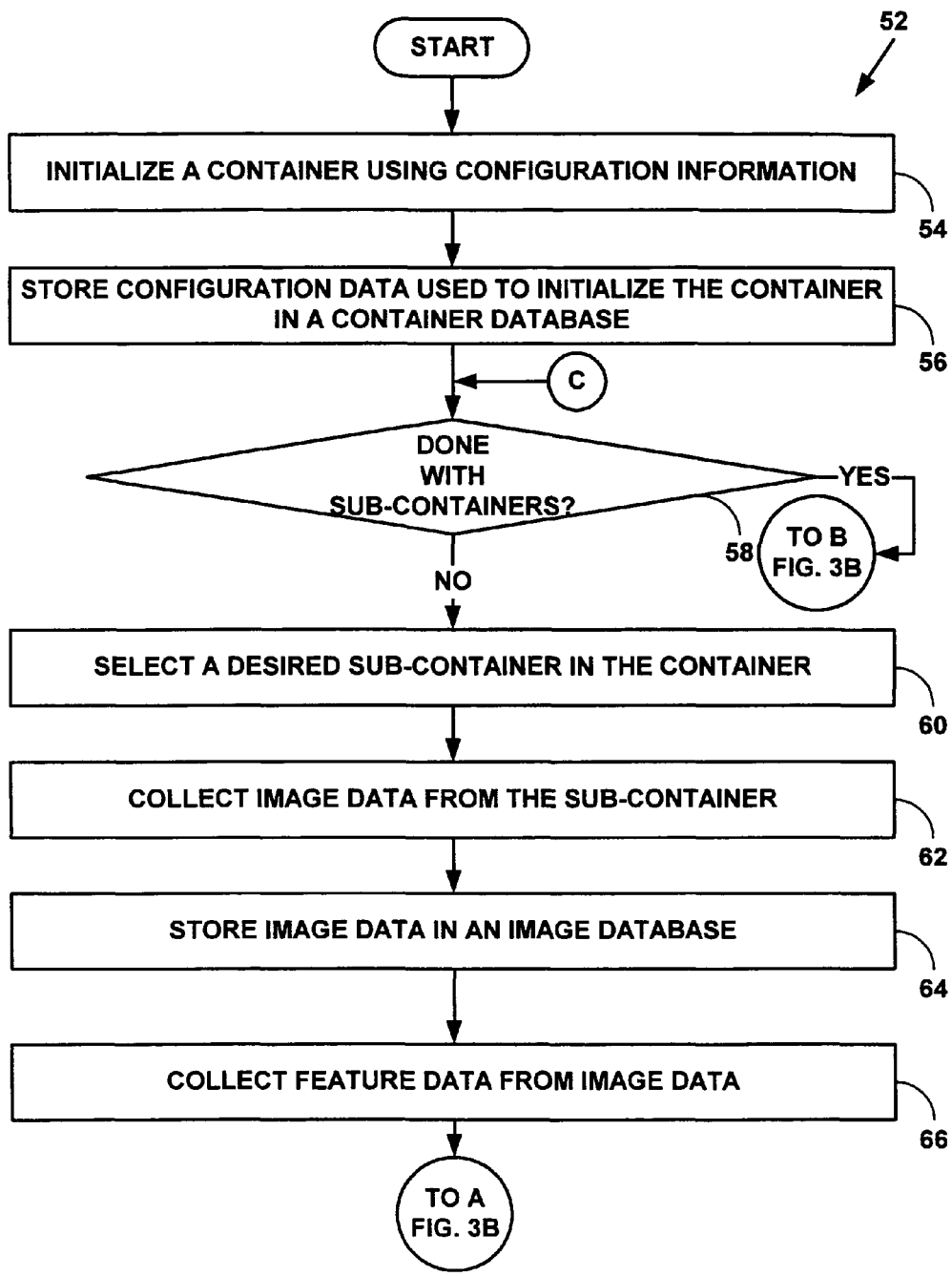

FIGS. 3A and 3B are a flow diagram illustrating a Method 52 for collecting experimental data. In FIG. 3A at Step 54, a container with multiple sub-containers is initialized using configuration information. At Step 56, the configuration information used for the container is stored in a container database. At Step 58, a loop is entered to repeat Steps 60, 62, 64, 66, 68, 70 and 72 for desired sub-containers in the container. At Step 60, a sub-container in the container is selected. In a preferred embodiment of the present invention, all of the sub-containers in a container are analyzed. In another embodiment of the present invention, less than all of the sub-containers in a container are analyzed. In such an embodiment, a user can select a desired sub-set of the sub-containers in a container for analysis. At Step 62, image data is collected from the sub-container. At Step 64, the image data is stored in an image database. At Step 66, feature data is collected from the image data.

In FIG. 3B at Step 68, the feature data is stored in a feature database. In one embodiment of the present invention, the image database and feature databases are combined into a single database comprising multiple tables including the image and feature data. In another embodiment of the present invention, the image database and feature databases are maintained as separate databases.

At Step 70, sub-container summary data is calculated. At Step 72, the sub-container summary data is stored in a sub-container database. In one embodiment of the present invention, the sub-container database and the container database are combined into a single database comprising multiple tables including the sub-container and container summary data. In another embodiment of the present invention, the sub-container and container databases are maintained as separate databases. The loop continues at Step 58 (FIG. 3A) until the desired sub-containers within a container have been analyzed. After the desired sub-containers have been processed in the container, the loop at Step 58 ends.

At Step 74 of FIG. 3B, container summary data is calculated using sub-container summary data from the sub-container database. At Step 76, the container summary data is stored in the container database.

In a general use of the invention, at Step 66 features from any imaging-based analysis system can be used. Given a digitized image including one or more objects (e.g., cells), there are typically two phases to analyzing an image and extracting feature data as feature measurements. The first phase is typically called "image segmentation" or "object isolation," in which a desired object is isolated from the rest of the image. The second phase is typically called "feature extraction," wherein measurements of the objects are calculated. A "feature" is typically a function of one or more measurements, calculated so that it quantifies a significant characteristic of an object. Typical object measurements include size, shape, intensity, texture, location, and others.

For each measurement, several features are commonly used to reflect the measurement. The "size" of an object can be represented by its area, perimeter, boundary definition, length, width, etc. The "shape" of an object can be represented by its rectangularity (e.g., length and width aspect ratio), circularity (e.g., perimeter squared divided by area, bounding box, etc.), moment of inertia, differential chain code, Fourier descriptors, etc. The "intensity" of an object can be represented by a summed average, maximum or minimum grey levels of pixels in an object, etc. The "texture" of an object quantifies a characteristic of grey-level variation within an object and can be represented by statistical features including standard deviation, variance, skewness, kurtosis and by spectral and structural features, etc. The "location" of an object can be represented by an object's center of mass, horizontal and vertical extents, etc. with respect to a predetermined grid system. For more information on digital image feature measurements, see: "Digital Image Processing," by Kenneth R. Castleman, Prentice-Hall, 1996, ISBN-0132114674, "Digital Image Processing: Principles and Applications," by G. A. Baxes, Wiley, 1994, ISBN-0471009490, "Digital Image Processing," by William K. Pratt, Wiley and Sons, 1991, ISBN-0471857661, or "The Image Processing Handbook—$2^{nd}$ Edition," by John C. Russ, CRC Press, 1991, ISBN-0849325161, the contents of all of which are incorporated by reference.

In one exemplary preferred embodiment of the present invention, Method 52 is used to collect cell image data and cell feature data from wells in a "microplate." In another preferred embodiment of the present invention, Method 52 is used to collect cell image and cell feature data from microgels in a bio-chip. As is known in the art, a "microplate" is a flat, shallow dish that stores multiple samples for analysis and typically includes 96 to 1536 individual wells. A "well" is a small area in a microplate used to contain an individual sample for analysis. Each well may be divided into multiple fields. A "field" is a sub-region of a well that represents a field of vision (i.e., a zoom level) for a photographic microscope. Each well is typically divided into one to sixteen fields. Each field typically will have between one and six photographic images taken of it, each using a different light filter to capture a different wavelength of light for a different fluorescence response for desired cell components. However, the present invention is not limited to such an embodiment, and other containers (e.g., varieties of biological chips, such as DNA chips, micro-arrays, and other containers with multiple sub-containers), sub-containers can also be used to collect image data and feature data from other than cells.

In an embodiment collecting cell data from wells in a microplate, at Step 54 a microplate with multiple wells is initialized using configuration information. At Step 56, the configuration information used for the microplate is stored in a microplate database. At Step 58, a loop is entered to repeat Steps 60, 62, 64, 66, 68, 70 and 72 for desired wells in the microplate. At Step 60, a well in the microplate is selected. At Step 62, cell image data is collected from the well. In one preferred embodiment of the present invention, the cell image data includes digital photographic images collected with a digital camera attached to a robotic microscope. However, other types of cameras can also be used and other types of image data can also be collected. At Step 64, the cell image data is stored in an image database. In another exemplary preferred embodiment of the present invention, the image database is a collection of individual image files stored in a binary format (e.g., Tagged Image File Format ("TIFF"), Device-Independent Bit map ("DIB") and others). The collection of individual image files may or may not be included in a formal database framework. The individual image files may exist as a collection of individual image files in specified directories that can be accessed from another database (e.g., a pass-through database).

At Step 66, cell feature data is collected from the cell image data. In one preferred embodiment of the present invention, Step 66 includes collecting any of the cell feature data illustrated in Table 1. However, other feature data and other cell feature can also be collected and the present invention is not limited to the cell feature data illustrated in Table 1. Virtually any feature data can be collected from the image data.

TABLE 1

CELL SIZE
CELL SHAPE
CELL INTENSITY
CELL TEXTURE
CELL LOCATION
CELL AREA
CELL PERIMETER
CELL SHAPE FACTOR
CELL EQUIVALENT DIAMETER
CELL LENGTH
CELL WIDTH
CELL INTEGRATED FLUORESCENCE INTENSITY
CELL MEAN FLUORESCENCE INTENSITY
CELL VARIANCE
CELL SKEWNESS
CELL KURTOSIS
CELL MINIMUM FLUORESCENCE INTENSITY
CELL MAXIMUM FLUORESCENCE INTENSITY
CELL GEOMETRIC CENTER
CELL X-COORDINATE OF A GEOMETRIC CENTER
CELL Y-COORDINATE OF A GEOMETRIC CENTER

In FIG. 3B at Step 68, the cell feature data is stored in a cell feature database. In one embodiment of the present invention, the image database and cell feature databases are combined into a single database comprising multiple tables including the cell image and cell feature data. In another embodiment of the present invention, the image database (or image files) and feature databases are maintained as separate databases.

Returning to FIG. 3B at Step 70, well summary data is calculated using the image data and the feature data collected from the well. In one preferred embodiment of the present invention, the well summary data calculated at Step 72 includes calculating any of the well summary data illustrated in Table 2. However, the present invention is not limited to the well summary data illustrated in Table 2, and the other sub-containers and other sub-container summary data can also be calculated. Virtually any sub-container summary data can be calculated for desired sub-containers. In Table 2, a "SPOT" indicates a block of fluorescent response intensity as a measure of biological activity.

TABLE 2

WELL CELL SIZES
WELL CELL SHAPES
WELL CELL INTENSITIES
WELL CELL TEXTURES
WELL CELL LOCATIONS
WELL NUCLEUS AREA
WELL SPOT COUNT
WELL AGGREGATE SPOT AREA
WELL AVERAGE SPOT AREA
WELL MINIMUM SPOT AREA
WELL MAXIMUM SPOT AREA
WELL AGGREGATE SPOT INTENSITY
WELL AVERAGE SPOT INTENSITY
WELL MINIMUM SPOT INTENSITY
WELL MAXIMUM SPOT INTENSITY
WELL NORMALIZED AVERAGE SPOT INTENSITY
WELL NORMALIZED SPOT COUNT
WELL NUMBER OF NUCLEI
WELL NUCLEUS AGGREGATE INTENSITY
WELL DYE AREA
WELL DYE AGGREGATE INTENSITY
WELL NUCLEUS INTENSITY
WELL CYTOPLASM INTENSITY
WELL DIFFERENCE BETWEEN NUCLEUS AND

TABLE 2-continued

CYTOPLASM INTENSITY
WELL NUCLEUS BOX-FILL RATIO
WELL NUCLEUS PERIMETER SQUARED AREA
WELL NUCLEUS HEIGHT/WIDTH RATIO
WELL CELL COUNT

Returning to FIG. 3B at Step 72, the well summary data is stored in a well database. In one embodiment of the present invention, the well database and the microplate database are combined into a single database comprising multiple tables including the well and microplate data. In another embodiment of the present invention, the well and microplate databases are maintained as separate databases. Returning to FIG. 3A, the loop continues at Step 58 (FIG. 3A) until the desired sub-wells within a microplate have been analyzed.

After the desired wells have been processed in the microplate, the loop at Step 58 ends. At Step 74 of FIG. 3B, summary data is calculated using well summary data from the microplate database. At Step 76, the microplate summary data is stored in the well database.

In one preferred embodiment of the present invention, the microplate summary data calculated at Step 74 includes calculating any of the microplate summary data illustrated in Table 3. However, the present invention is not limited to the microplate summary data illustrated in Table 3, and other container and other container summary data can also be calculated. Virtually any container summary data can be calculated for a container. In Table 3, "MEAN" indicates a statistical mean and "STDEV" indicates a statistical standard deviation, known in the art, and a "SPOT" indicates a block of fluorescent response intensity as a measure of biological activity.

TABLE 3

MEAN SIZE OF CELLS
MEAN SHAPES OF CELLS
MEAN INTENSITY OF CELLS
MEAN TEXTURE OF CELLS
LOCATION OF CELLS
NUMBER OF CELLS
NUMBER OF VALID FIELDS
STDEV NUCLEUS AREA
MEAN SPOT COUNT
STDEV SPOT COUNT
MEAN AGGREGATE SPOT AREA
STDEV AGGREGATE SPOT AREA
MEAN AVERAGE SPOT AREA
STDEV AVERAGE SPOT AREA
MEAN NUCLEUS AREA
MEAN NUCLEUS AGGREGATE INTENSITY
STDEV AGGREGATE NUCLEUS INTENSITY
MEAN DYE AREA
STDEV DYE AREA
MEAN DYE AGGREGATE INTENSITY
STDEV AGGREGATE DYE INTENSITY
MEAN MINIMUMSPOT AREA
STDEV MINIMUM SPOT AREA
MEAN MAXIMUM SPOT AREA
STDEV MAXIMUM SPOT AREA
MEAN AGGREGATE SPOT INTENSITY
STDEV AGGREGATE SPOT INTENSITY
MEAN AVERAGE SPOT INTENSITY
STDEV AVERAGE SPOT INTENSITY
MEAN MINIMUM SPOT INTENSITY
STDEV MINIMUM SPOT INTENSITY
MEAN MAXIMUM SPOT INTENSITY
STDEV MAXIMUM SPOT INTENSITY
MEAN NORMALIZED AVERAGE SPOT INTENSITY
STDEV NORMALIZED AVERAGE SPOT INTENSITY
MEAN NORMALIZED SPOT COUNT

TABLE 3-continued

STDEV NORMALIZED SPOT COUNT
MEAN NUMBER OF NUCLEI
STDEV NUMBER OF NUCLEI
NUCLEI INTENSITIES
CYTOPLASM INTENSITIES
DIFFERENCE BETWEEN NUCLEI AND
CYTOPLASM INTENSITIES
NUCLEI BOX-FILL RATIOS
NUCLEI PERIMETER SQUARED AREAS
NUCLEI HEIGHT/WIDTH RATIOS
WELL CELL COUNTS

In one exemplary preferred embodiment of the present invention, cell assays are created using selected entries from Tables 1-3. In a preferred embodiment of the present invention, a "cell assay" is a specific implementation of an image processing method used to analyze images and return results related to biological processes being examined. For more information on the image processing methods used in cell assays targeted to specific biological processes, see co-pending application Ser. Nos. 09/031,217 and 09/352,171, assigned to the same Assignee as the present application, and incorporated herein by reference.

In one exemplary preferred embodiment of the present invention, the microplate and well databases are stored in a single database comprising multiple tables called "SYSTEM.MDB." The image and feature data for each well is stored in separate databases in the format "ID.MDB," where ID is a unique identifier for a particular scan. However, the present invention is not limited to this implementation, and other types, and more or fewer databases can also be used.

Storing Experimental Data

FIG. 4 is a flow diagram illustrating a Method 78 for storing collected experimental data. At Step 80, image data and feature data is collected from desired sub-containers in a container (e.g., with Method 52 of FIG. 3). At Step 82, a first database is created. The first database includes links to other databases but does not include any data collected from the container. The first database is used as a "pass-through" database by a display application to view data collected from a container. At Step 84, a first entry is created in the first database linking the first database to a second database. The second database includes configuration data used to collect data from the container, summary data for the container calculated from the desired sub-containers and summary data for the desired sub-containers in the container calculated from the image data and feature data. The information is organized in multiple database tables in the second database. At Step 86, multiple second entries are created in the first database linking the first database to multiple third databases. The multiple third databases include image data and feature data collected from the desired sub-containers in the container. The data is organized in multiple database tables in the third database.

In one exemplary preferred embodiment of the present invention, at Step 80, image data and feature data is collected from desired wells in a microplate using Method 52 of FIG. 3. However, the present invention is not limited to using Method 52 to collect experimental data and other methods can also be used. In addition, the present invention is not limited to collecting image data and feature data from wells in a microplate and other sub-containers and containers can also be used (e.g., bio-chips with multiple micro-gels).

At Step 82, an application database is created. In one exemplary preferred embodiment of the present invention, the application database includes links to other databases but does not include any data collected from the microplate. The application database is used by a display application to view data collected from a microplate. In another embodiment of the present invention, the application database may include actual data.

Figure 5:
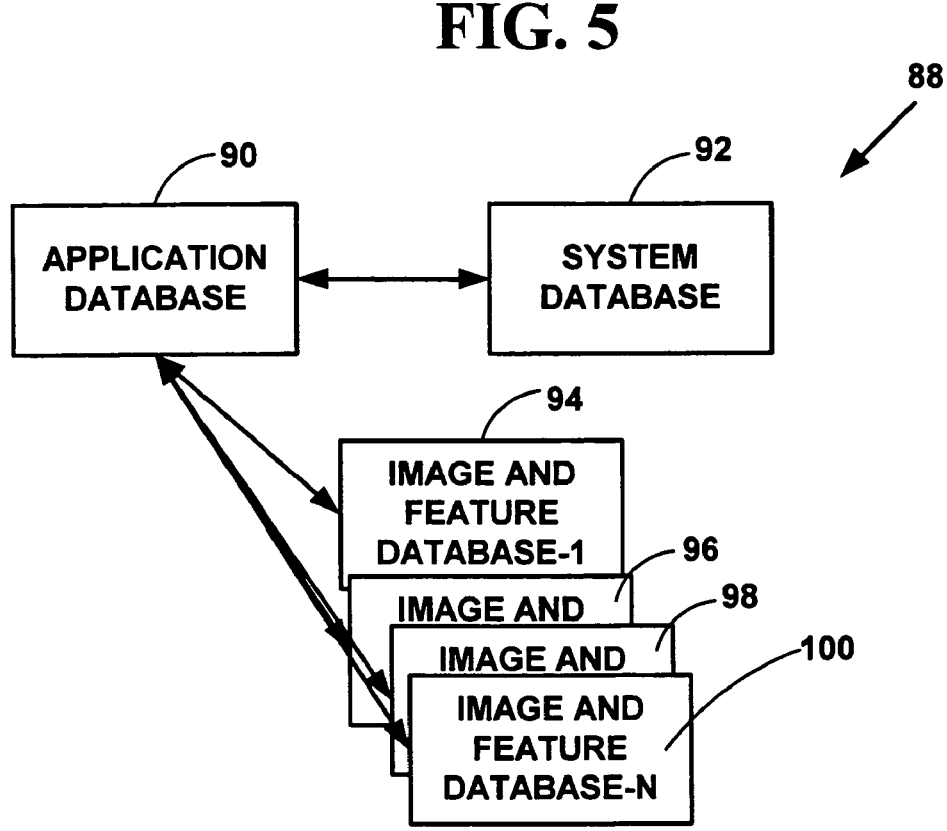
FIG. 5 is a block diagram illustrating an exemplary database system for the method of FIG. 4.

FIG. 5 is a block diagram illustrating an exemplary database system 88 for Method 78 of FIG. 4. The database system 88 includes an application database 90, a system database 92 and multiple image and feature databases 94, 96, 98, 100. FIG. 5 illustrates only four image and feature databases numbered 1-N. However, the present invention is not limited to four image and features databases and typically hundreds or thousands of individual image and feature databases may actually be used. In addition the present invention is not limited to the databases or database names illustrated in FIG. 5 and more or fewer databases and other database names may also be used.

In one exemplary preferred embodiment of the present invention, the application database 90 is called "APP.MDB." However, other names can also be used for the application database in the database system and the present invention is not limited to the name described.

In one exemplary preferred embodiment of the present invention, a display application used to display and analyze collected experimental does not access over a few thousand records at one time. This is because there is no need for evaluation of microplate detail data information (e.g., image or cell feature database data) across microplates. Summary microplate information is stored in microplate, well, microplate eature and well feature summary tables to be compared across microplates. Detailed information about individual cells is accessed within the context of evaluating one microplate test. This allows a display application to make use of pass-through tables in the application database 90.

In a preferred embodiment of the present invention, the application database 90 does not contain any actual data, but is used as a "pass-through" database to other databases that do contain actual data. As is known in the art, a pass-through database includes links to other databases, but a pass-through database typically does not contain any actual database data. In such and embodiment, the application database 90 uses links to the system database 92 and the multiple image and feature databases 94, 96, 98, 100 to pass-through data requests to the application database 90 to these databases. In another exemplary preferred embodiment of the present invention, the application database 90 may include some of the actual data collected, or summaries of actual data collected. In one exemplary preferred embodiment of the present invention, the application database 90 is a Microsoft Access database, a Microsoft Structured Query Language ("SQL") database or Microsoft SQL Server by Microsoft of Redmond, Wash. However, other databases such as Oracle databases by Oracle Corporation of Mountain View, Calif., could also be used for application database 90, and the present invention is not limited to Microsoft databases.

In another preferred embodiment of the present invention, a first pass-through database is not used at all. In such an embodiment, the first pass-through database is replaced by computer software that dynamically "directs" queries to/from the second and third databases without actually creating or using a first pass-through database.

Figure 6:
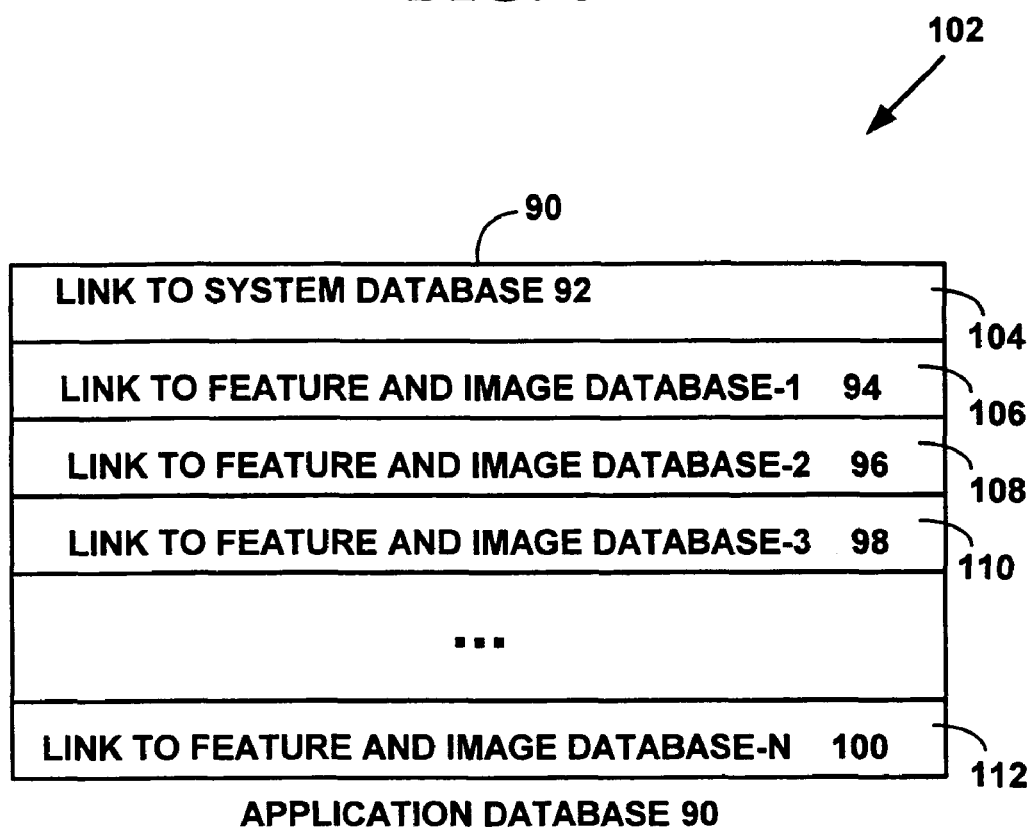
FIG. 6 is a block diagram illustrating an exemplary database table layout in an application database of FIG. 5.

FIG. 6 is a block diagram illustrating an exemplary database table layout 102 for the application database 90 of FIG. 5. The database table layout 102 of FIG. 6 includes a first pass-through database entry 104 linking the application database 90 to the system database 92. The database table layout also includes multiple second pass through database entries 106, 108, 110, 112 linking the application database to multiple image and feature databases 94, 96, 98, 100. However, more or fewer types of database entries can also be used in the application database, and the present invention is not limited to two types of pass-through databases entries. In another embodiment of the present invention, the application database 92 may also include experimental data (not illustrated in FIG. 6).

Returning to FIG. 4 at Step 84, a first entry is created in the application database 90 linking the application database 90 to a system database 92 (e.g., box 104, FIG. 6). The system database 92 includes configuration data used to collect data from a microplate, summary data for the microplate calculated from the desired wells and summary data for selected wells in the microplate calculated from the image data and feature data. This information is organized in multiple tables in the system database 92.

In one exemplary preferred embodiment of the present invention, the system database 92 is called "SYSTEM.MDB." However, other names could also be used and the present invention is not limited to this name. The system database 92 may also be linked to other databases including microplate configuration and microplate summary data and is used in a pass-through manner as was described above for the application database. In another exemplary preferred embodiment of the present invention, the system database 92 is not linked to other databases, but instead includes actual microplate configuration and microplate summary data in multiple internal tables.

However, in either case, in one preferred embodiment of the present invention, the name of the system database 92 is not changed from microplate-to-microplate. In another preferred embodiment of the present invention, the name of the system database 92 is changed from microplate-to-microplate. A display application will refer to the system database 92 using its assigned name (e.g., SYSTEM.MDB) for microplate configuration and microplate summary data. Data stored in the system database 92 may be stored in linked databases so that the actual microplate container configuration and microplate summary data can be relocated without changing the display application accessing the system database 92. In addition the actual database engine could be changed to another database type, such as a Microsoft SQL Server or Oracle databases by Oracle, or others without modifying the display application accessing the system database 92.

Figure 7:
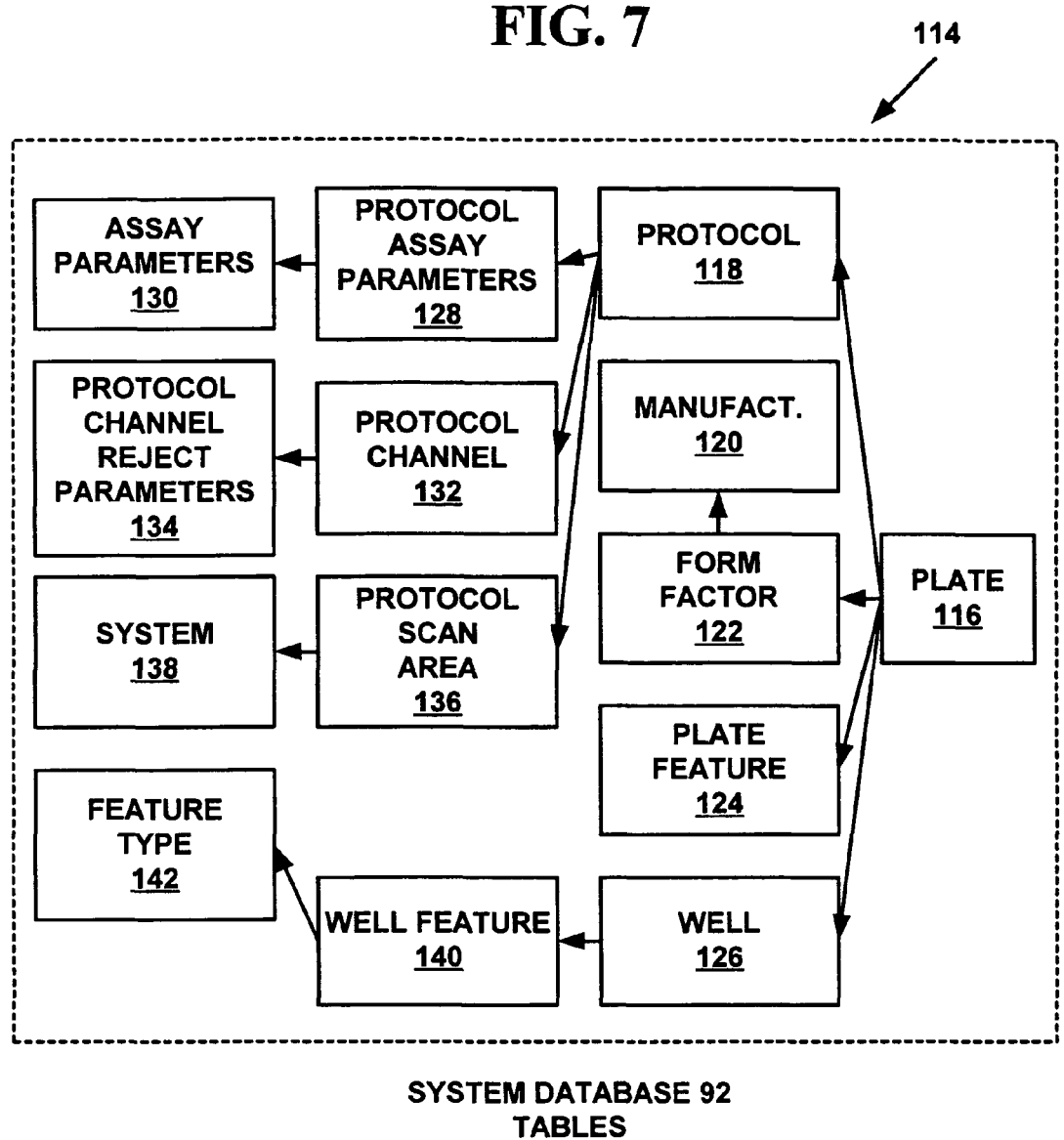
FIG. 7 is a block diagram illustrating an exemplary database tables in a system database of FIG. 5.

FIG. 7 is a block diagram illustrating exemplary database tables 114 for the system database 92 of FIG. 5. The database table, 114 of FIG. 7 includes a plate table 116 that includes a list of plates being used. The plate table 116 is linked to a protocol table 118, a form factor table 122, a plate feature table 124 and a well table 126. The protocol table 118 includes protocol information. In a preferred embodiment of the present invention, a protocol specifies a series of system settings including a type of analysis instrument, an assay, dyes used to measure biological markers cell identification parameters and other parameters used to collect experimental data. An assay is described below. The form factor table 122 includes microplate layout geometry. For example, a standard 96-well microplate includes 12 columns of wells labeled 1 through 12 and 8 rows of wells labeled A through H for a total of 96. The plate feature table 124 includes a mapping of features to microplates. The form factor table 122 is liked to the manufacturer table 120. The manufacturer table 120 includes a list microplate manufactures and related mircoplate information. The well table 126 includes details in a well. In a preferred embodiment of the present invention, a well is a small area (e.g., a circular area) in a microplate used to contain cell samples for analysis.

The protocol table 118 is linked to a protocol assay parameters table 128. In a preferred embodiment of the present invention, an "assay" is a specific implementation of an image processing method used to analyze images and return results related to biological processes being examined. The protocol assay parameters table 128 is linked to an assay parameters table 130. The assay parameters table 130 include parameters for an assay in use.

The protocol table 118 is also linked to a protocol channel table 132. Typically an assay will have two or more channels. A "channel" is a specific configuration of optical filters and channel specific parameters and is used to acquire an image. In a typical assay, different fluorescent dyes are used to label different cell structures. The fluorescent dyes emit light at different wavelengths. Channels are used to acquire photographic images for different dye emission wavelengths. The protocol channel table 132 is linked to a protocol channel reject parameters table 134. The protocol channel reject parameters table 134 includes channel parameters used to reject images that do not meet the desired channel parameters.

The protocol table 118 is also linked to a protocol scan area table 136. The protocol scan area table 136 includes methods used to scan a well. The protocol scan area table 136 is linked to a system table 138. The system table 138 includes information configuration information and other information used to collect experimental data.

The well table 126 is linked to a well feature table 140. The well feature table 140 includes mapping of cell features to wells. The well feature table 140 is linked to a feature type table 142. The feature type table 142 includes a list of features (e.g., cell features) that will be collected. However, more or fewer tables can also be used, more or fewer links can be used to link the tables, and the present invention is not limited to the tables described for the system database 92.

Returning to FIG. 4 Step 86, multiple second entries (e.g., boxes 106, 108, 110, 112 of FIG. 6) are created in the application database 92 linking the application database 92 to multiple image and feature databases 94, 96, 98, 100. The multiple image and feature databases include image data and feature data collected from the desired wells in the microplate. The data is organized in multiple database tables in the image and feature databases.

In one exemplary preferred embodiment of the present invention, names of image and feature databases 94, 96, 98, 100 that contain the actual image and feature data are changed dynamically from microplate-to-microplate. Since the image and feature data will include many individual databases, an individual image and feature database is created when a microplate record is created (e.g., in the plate table 116 (FIG. 7) in the system database 92 (FIG. 5)) and has a name that is created by taking a plate field value and adding ".MDB" to the end. (For example, a record in a plate table 116 with a field identifier of "1234569803220001" will have it's data stored in a image and feature database with the name "1234569803220001.MDB"). However, other names can also be used for the image and feature databases and the present invention is not limited to the naming scheme using a field identifier from the plate table 116.

Figure 8:
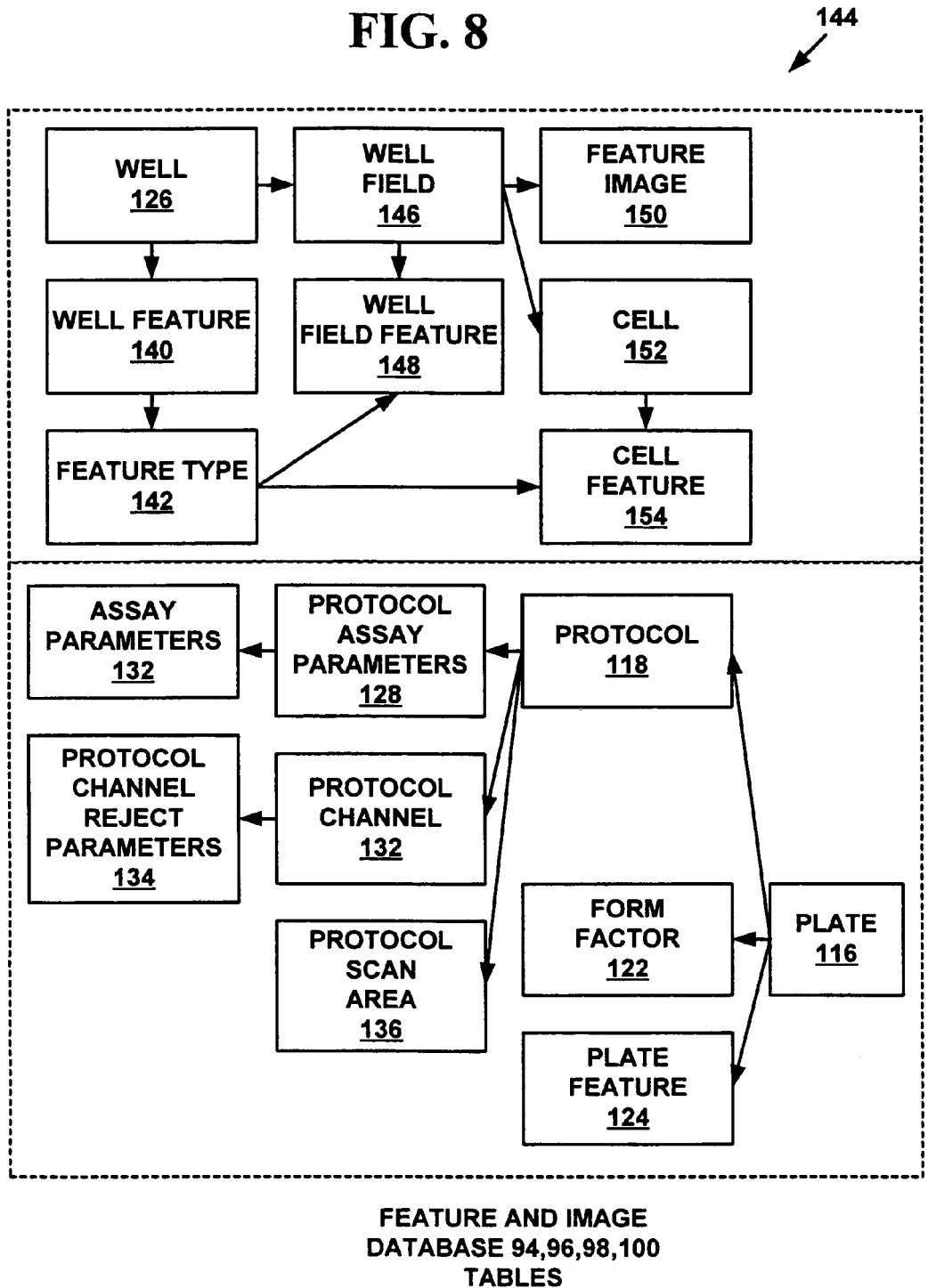
FIG. 8 is a block diagram illustrating an exemplary database tables in an image and feature database of FIG. 5.

FIG. 8 is a block diagram illustrating exemplary database tables 144 for image and feature databases 94, 96, 98, 100 of FIG. 5. In one preferred embodiment of the present invention, the image and feature databases for a microplate include tables to hold image and feature data and a copy of the tables 116-142 (FIG. 7) excluding the manufacturer table 120 and the system table 138 used for the system database 92. In another embodiment of the present invention, the image and feature databases 94, 96, 98, 100 include a copy or all of the tables 116-142 (FIG. 7). In another embodiment of the present invention, the image and feature databases 94, 96, 98, 100 do not include a copy of the tables 116-142 (FIG. 7) used for the system database 92. However, having a copy of the system database 92 tables in the image and feature databases allows individual image and feature databases to be archived and copied to another data storage system for later review and thus aids analysis.

The image and feature databases 94, 96, 98, 100, tables 144 include a well field table 146 for storing information about fields in a well. The well field table 146 is linked to a well feature table 148 that includes information a list of features that will be collected from a well. The well field table 146 is also linked to a feature image table 150 that includes a list of images collected from a well and a cell table 152 that includes information to be collected about a cell. The cell table 152 is linked to a cell feature table 154 that includes a list of features that will be collected from a cell. However, more or fewer tables can also be used, more or fewer links can be used to link the tables, and the present invention is not limited to the tables described for the image and feature databases.

Spooling Experimental Data

As was discussed above, the analysis instruments modules 12, 14, 16 generate a large amount of data including image data, feature data, and summary data for sub-containers and containers. The raw feature data values are stored as database files with multiple tables described above (e.g., FIG. 8). To prevent analysis instruments 12, 14, 16 and/or the store clients 18, 20, 22 from running out of file space, database files are managed using a hierarchical data management system.

Figure 9:
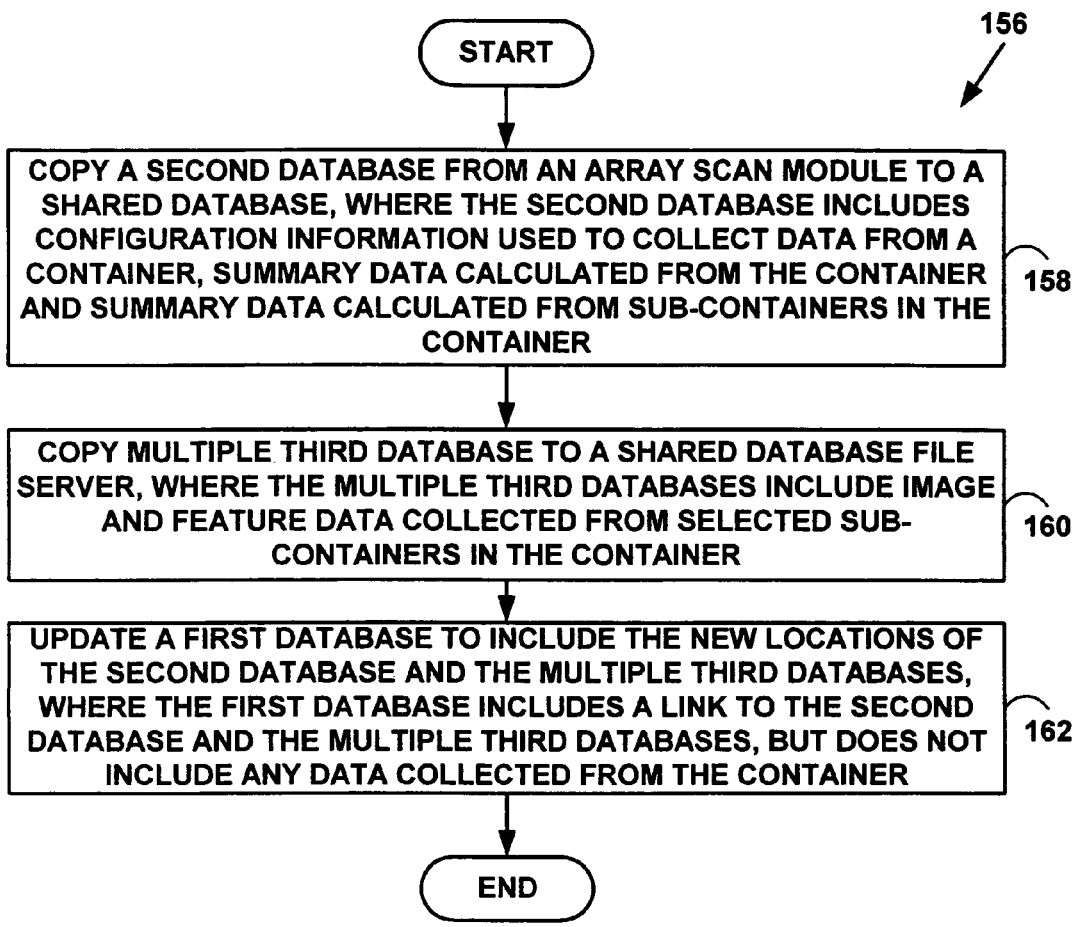
FIG. 9 is a flow diagram illustrating a method for spooling experimental data.

FIG. 9 is a flow diagram illustrating a Method 156 for spooling experimental data. At Step 158, a second database is copied from an analysis instrument to a shared database. The second database includes configuration data used to collect data from a container, summary data for the container calculated from one or more sub-containers in the container and summary data for sub-containers in the container calculated from image data and feature data collected from desired sub-containers. The data in the second database is organized into one or more database tables. At Step 160, multiple third databases are copied to a shared database file server. The multiple third databases include image data and a feature data collected from the desired sub-containers in the container. The data in the third database is organized into one or more database tables. At Step 162, a location of the second database and the one or more third databases is updated in a first database on the analysis instrument to reflect new storage locations for the second database on the shared database and one or more third databases on the shared database file server. The first database includes links to the second database and the one or more third databases but does not include any data collected from the container. The first database is used by a display application to view data collected from a container.

In another preferred embodiment of the present invention, Method 156 further comprises copying the first database from the analysis instruments 12, 14, 16 to a store client computers 18, 20, 22. Such an embodiment allows a display application on the store client computers 18, 20, 22 to view the data collected from the container using the first database copied to local storage on the client computers 18, 20, 22.

In another preferred embodiment of the present invention, Method 156 further comprises locating the first database on the analysis instruments 12, 14, 16 from store client computers 18, 20, 22. Such an embodiment allows a display application on the store client computers 18, 20, 22 to view the data collected from the container at a remote location on the exemplary data storage system 10' from the store client computers 18, 20, 22.

The data collected is viewed from the display application on the store client computers 18, 20, 22 by retrieving container and sub-container data from the second database on the shared database 24 and image and feature data from the multiple third databases on the shared database file server 28.

In one exemplary preferred embodiment of the present invention, at Step 158, a system database 92 (FIG. 5) is copied from an analysis instrument 12, 14, 16 to the shared database 24. The system database 92 includes configuration data used to collect data from a microplate, summary data for the microplate calculated from one or more wells in the microplate (e.g., Table 3) and summary data for wells in the microplate (e.g., Table 2) calculated from image data and feature data (e.g., Table 1) collected from desired wells as was described above. The data in the system database 92 is organized into one or more database tables (e.g., FIG. 7).

At Step 160, one or more image and feature databases 94, 96, 98, 100 are copied to the shared database file server 28. The one or more image and feature databases 94, 96, 98, 100 include image data and a feature data collected from the desired wells in the microplate. The data in the one or more image and feature databases is organized into one or more database tables (e.g., FIG. 8).

At Step 162, a location of the system database 92 and the one or more image and feature databases 94, 96, 98, 100 is updated in an application database 90 (FIG. 6) on the analysis instrument 12, 14, 16 to reflect new storage locations for the system database 92 on the store database 24 and one or more image and feature databases 94, 96, 98, 100 on the store archive 28.

In one preferred embodiment of the present invention, the application database 90 is a pass-through database that includes links (e.g., FIG. 6) to the system database 92 and the one or more image and feature databases 94, 96, 98, 100 but does not include any data collected from the microplate. In another embodiment of the present invention, the application database 90 includes data from the microplate. The application database 92 is used by a display application to view data collected from a microplate. However, the present invention is not limited to this embodiment and other containers, sub-containers, (e.g., bio-chips with multiple micro-gels) and databases can also be used.

Hierarchical Management of Experimental Data

Figure 10:
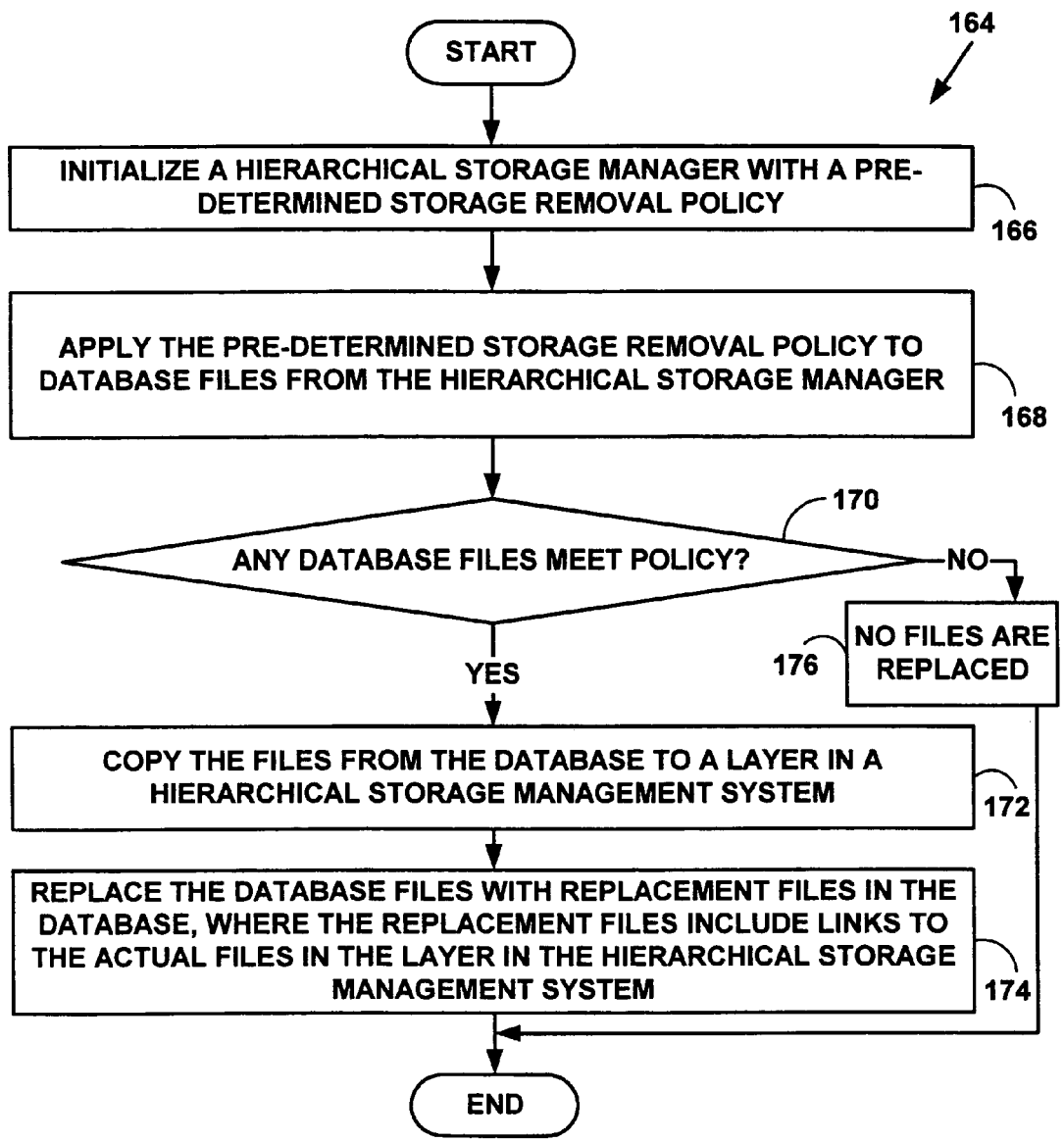
FIG. 10 is a flow diagram illustrating a method for hierarchical management experimental data.

FIG. 10 is a flow diagram illustrating a Method 164 for hierarchical management of experimental data. At Step 166, a hierarchical storage manager is initialized with a pre-determined storage removal policy. At Step 168, the hierarchical storage manager applies the pre-determined storage removal policy to database files in a database. At Step 170, a test is conducted to determine whether any database files on the database match the pre-determined storage removal policy. If any database files in the database match the pre-determined storage removal policy, at Step 172, the database files are copied from the database to a layer in a hierarchical store management system. At Step 174, database files in the database are replaced with placeholder files. The placeholder files include links to the actual database files copied to the layer in the hierarchical store management system. If no database files in the database match the pre-determined storage removal policy, at Step 176, no database files are copied from the database to a layer in a hierarchical store management system.

In one exemplary preferred embodiment of the present invention, the pre-determined storage removal policy includes one or more rules illustrated by Table 4. However, more or fewer storage removal policy rules can also be used and the present invention is not limited to storage removal policy rules illustrated in Table 4.

TABLE 4

PERCENTAGE OF DISK SPACE AVAILABLE
OR PERCENTAGE OF DISK SPACE USED.
NUMBER OF FILES.
DATE A FILE IS STORED.
SIZE OF A FILE.
NUMBER OF DAYS SINCE A FILE WAS LAST ACCESSED.
FILE TYPE.
FILE NAME.

Method 164 includes HSM steps that provide a method to allow on-line access to virtually unlimited amounts of "virtual" disk space on data storage system 10'. The virtual disk space is provided with a multi-layer hierarchical storage management system. The virtual disk space is provided without changing the layout of any database and is "invisible" to a user.

In one exemplary preferred embodiment of the present invention, the HSM steps of Method 164 provide an archival method that implements a three-layer storage hierarchy including the disk archive 32, the optical jukebox 34 and the tape drive 36. However, more or fewer layers of storage can also be used and the present invention is not limited to HSM techniques with three-layer storage. Additional storage layers in the storage hierarchy are added as needed without changing the layout of any database or the functionality of the hierarchical storage manager. The hierarchical storage manager can copy database files to layers in an N-layer storage hierarchy without modification.

In addition, virtually unlimited amounts of "virtual" disk space can be provided with a three-layer hierarchical storage management system by periodically removing re-writeable optical disks, from the optical jukebox 34 and tapes from the tape drive 36 when these storage mediums are filled with data. The re-writeable optical disks and tapes are stored in a data library for later access. In another preferred embodiment of the present invention, the data library is directly accessible from computer network 40.

In a preferred embodiment of the present invention, Method 164 supports at least two modes of database file archiving. However, more or fewer modes of database archiving can also be used and the present invention is not limited to the two modes described.

In the first mode, the store server 26 retains database files on individual analysis instruments 12, 14, 16, where they were originally generated. The store server 26 uses Method 164 to automatically manage the free space on the analysis instrument 12, 14, 16 disks to move files into a layer in the three-tiered storage management system. To the end user the files will appear to be in the same directories where they were originally stored. However, the files may actually be stored on the disk archive 32, the optical jukebox 34, or in a Digital Linear Tape ("DLT") 36 library.

In the second mode, the store server 26 spools database files from the analysis instruments 12, 14, 16, to the shared database 24 and the shared database file server 30 (e.g., using Method 156). The store server's 26 in turn manages database files on the shared database file server 30 using Method 164. In the second mode, the files may also be stored on the disk archive 32, the optical jukebox 34, or in a DLT 36 library.

Experimental Data Presentation

As was discussed above, an analysis instrument 12, 14, 16 can generate a huge amount of experimental data. To be useful, the experimental data has to be visually presented to a scientist or technician for analysis.

Figure 11:
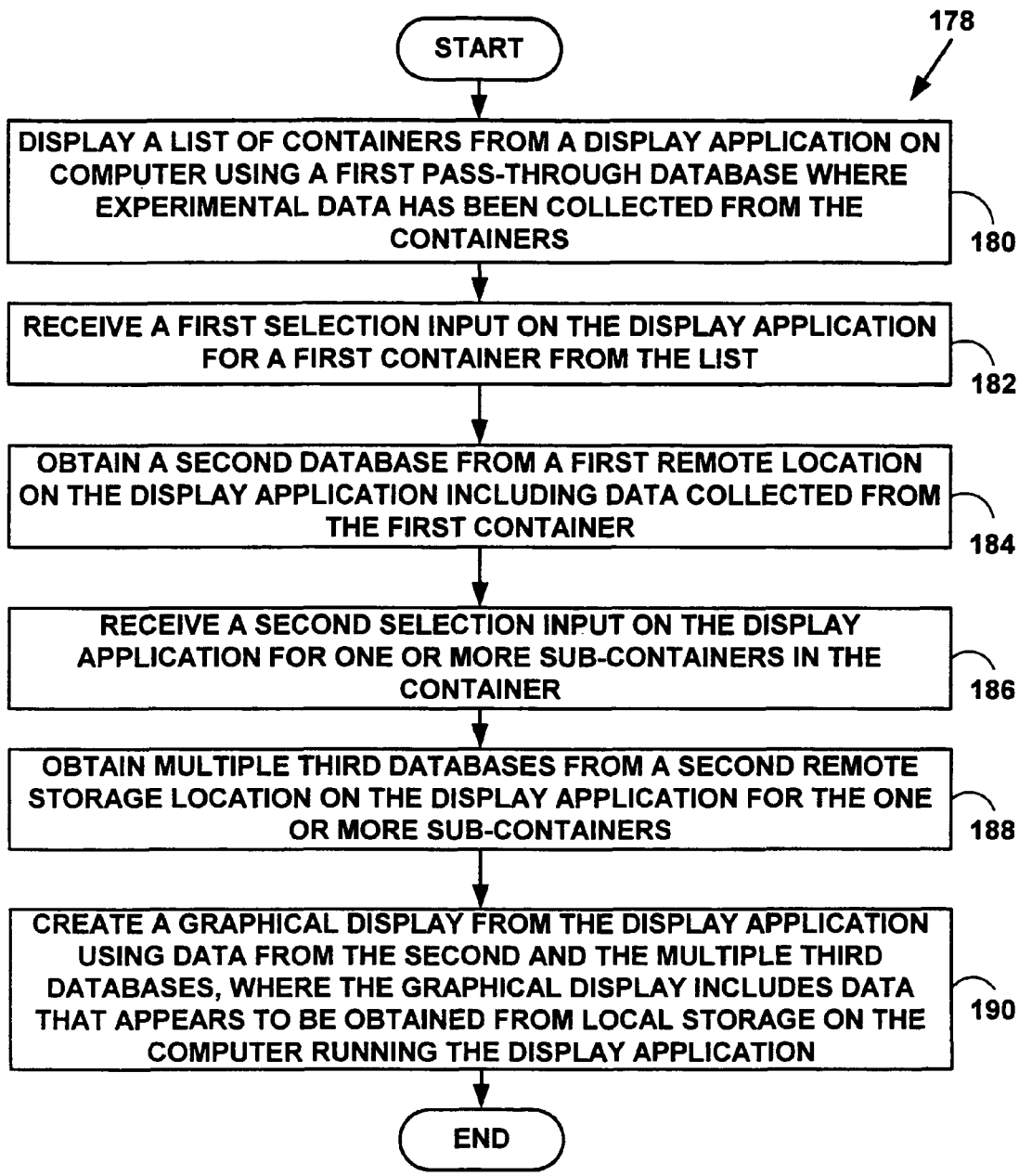
FIG. 11 is a flow diagram illustrating a method for presenting experimental data.

FIG. 11 is a flow diagram illustrating a Method 178 for presenting experimental data. At Step 180, a list including one or more containers is displayed using a first database from a display application on a computer. The containers include multiple sub-containers. Image data and feature data was collected from the one or more containers. The first database is a pass-through database including links to other databases with experimental data. At Step 182, a first selection input is received on the display application for a first container from the list. At Step 184, a second database is obtained for the first container from a first remote storage location. The first remote location is remote to the computer running the display application. The second database includes configuration data used to collect data from the first container, summary data for the first container calculated from the sub-containers in the first container and summary data for desired sub-containers in the first container calculated from image data and feature data collected from desired sub-containers. At Step 186, a second selection input is received on the display application for one or more sub-containers in the first container. At Step 188, multiple third databases are obtained from a second remote storage location. The multiple third databases include image data and feature data collected from the one or more sub-containers in the first container. At Step 190, a graphical display is created from the display application including container and sub-container data from the second database, image data and feature data from the multiple third databases collected from the one or more sub-containers. Data displayed on the graphical display will appear to be obtained from local storage on the computer instead of the first remote storage location and the second remote storage location.

In one exemplary preferred embodiment of the present invention, Method 178 is used for displaying experimental data collected from microplates with multiple wells. However, the present invention is not limited to this embodiment and can be used for other containers and sub-containers besides microplates with multiple wells (e.g., bio-chips with multiple micro-gels).

In such an exemplary embodiment at Step 180, a list including multiple microplates is displayed from a display application on a computer. The microplates include multiple wells. Cell image data and cell feature data were collected from the multiple microplates. The display application uses an application database 90 to locate other databases, including experimental data.

In one preferred exemplary embodiment of the present invention, the application database 90 is located on the exemplary data storage system 10' at a location remote from the computer including the display application. The application database 90 is used from the computer including the display application without copying the application database 90 from a remote location on the exemplary data storage system 10'.

In another exemplary preferred embodiment of the present invention, the application database 90 is copied from a location on the exemplary data storage system 10' to local storage on the computer including the display application. In such an embodiment, the application database 90 is copied to, and exists on the computer including the display application.

At Step 182, a first selection input is received on the display application for a first microplate from the list. At Step 184, a system database 92 is obtained for the first microplate from a first remote storage location. The first remote storage location is remote to the computer running the display application. The system database 92 includes configuration data used to collect data from the first microplate summary data for the first microplate calculated from the wells in the first microplate and summary data for desired wells in the first microplate calculated from image data and feature data collected from desired wells.

At Step 186, a second selection input is received on the display application for one or more wells in the first microplate. At Step 188, multiple image and feature databases 94, 96, 98, 100 are obtained from a second remote storage location. The multiple image and feature databases 94, 96, 98, 100 include image data and feature data collected from the one or more wells in the first microplate. At Step 190, a graphical display is created from the display application including microplate and well summary data from the system database 92, image data and feature data from the multiple image and feature databases 94, 96, 98, 100 collected from the one or more wells. Data displayed on the graphical display appears to be obtained from local storage on the computer instead of the first remote storage location and the second remote storage location.

Figure 12:
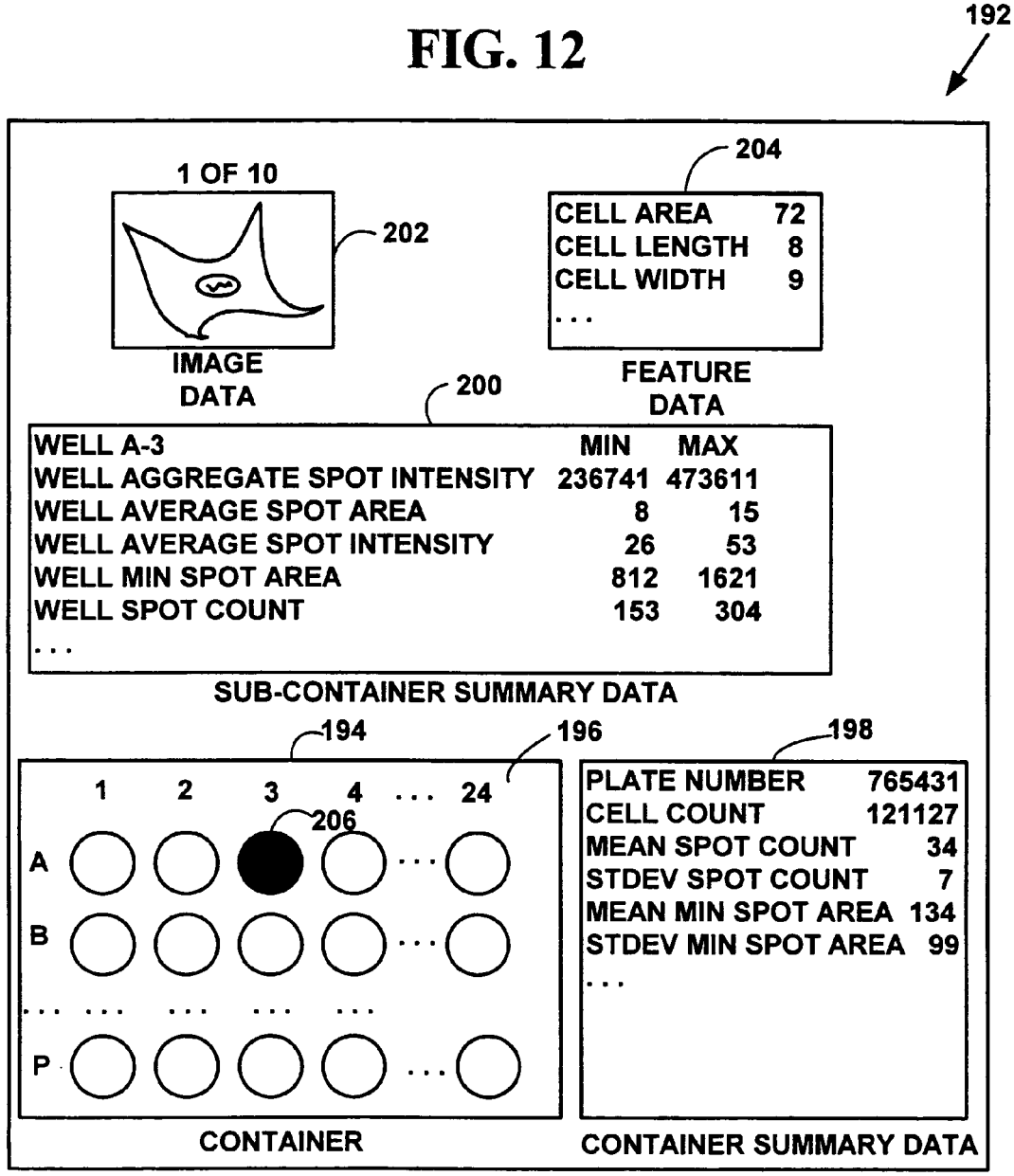
FIG. 12 is a block diagram illustrating a screen display for graphically displaying experimental data.

FIG. 12 is a block diagram illustrating an exemplary screen display 192 for visually displaying experimental data from a display application. The screen display 192 includes a display of multiple sub-containers 194 in a container 196. The container 194 includes 384 sub-containers (numbers 1-24×letters A-P or 24×16=384). The screen display 192 also includes container summary data 198, sub-container summary data 200, image data 202, and feature data 204. The screen display 192 is capable of displaying the data in both graphical formats and textual formats depending on user preferences. A user can select his/her display preferences from menus created by the display application (Not illustrated in FIG. 12). Screen display 192 illustrates exemplary data for sub-container A-3 illustrated by the blacked sub-container 206 in the container 196. Experimental data collected from a container is visually presented to a scientist or lab technician for analysis using Method 178 and screen display 192 with a pass-through database with multiple links to multiple databases from multiple remote locations.

In one exemplary preferred embodiment of the present invention, a Store Application Programming Interface ("API") is provided to access and use the methods and system described herein. As is known in the art, an API is set of interface routines used by an application program to access a set of functions that perform a desired task.

In one specific exemplary preferred embodiment of the present invention, the store API is stored in a Dynamic Link Library ("DLL") used with the Windows 95/98/NT/2000 operating system by Microsoft. The DLL is called "mvPlateData.DLL" However, the present invention is not limited to storing an API in a Window's DLL or using the described name of the DLL and other methods and names can also be used to store and use the API. As is known in the art, a DLL is library that allows executable routines to be stored and to be loaded only when needed by an application. The Store API in a DLL is registered with the Window's "REGSVR32.EXE" application to make it available to other applications. The Store API provides an interface access to plate, well image and cell feature information and provides a facility to enter desired well feature information that will be collected.

These methods and system described herein may allow experimental data from high-throughput data collection/analysis systems to be efficiently collected, stored, managed and displayed. The methods and system can be used for, but is not limited to storing managing and displaying cell image data and cell feature data collected from microplates including multiple wells or bio-chips including multiple micro-gels in which an experimental compound has been applied to a population of cells. If bio-chips are used, any references to microplates herein, can be replaced with bio-chips, and references to wells in a microplate can be replaced with micro-gels on a bio-chip and used with the methods and system described.

The methods and system may provide a flexible and scalable repository of cell data that can be easily managed and allows cell data to be analyzed, manipulated and archived. The methods and system may improve the identification, selection, validation and screening of new experimental compounds which have been applied to populations of cells. The methods and system may also be used to provide new bioinformatic techniques used to make observations about cell data.

It should be understood that the programs, processes, methods and systems described herein are not related or limited to any particular type of computer or network system (hardware or software), unless indicated otherwise. Various types of general purpose or specialized computer systems may be used with or perform operations in accordance with the teachings described herein.

In view of the wide variety of embodiments to which the principles of the present invention can be applied, it should be understood that the illustrated embodiments are exemplary only, and should not be taken as limiting the scope of the present invention.

For example, the steps of the flow diagrams may be taken in sequences other than those described, and more or fewer elements may be used in the block diagrams. While various elements of the preferred embodiments have been described as being implemented in software, in other embodiments in hardware or firmware implementations may alternatively be used, and vice-versa.

The claims should not be read as limited to the described order or elements unless stated to that effect. Therefore, all embodiments that come within the scope and spirit of the following claims and equivalents thereto are claimed as the invention.

We claim:

1. A method of collecting experimental data comprising the steps of:

initializing a container using configuration information, the container having a plurality of subcontainers disposed therein or thereon, each subcontainer having a biological specimen disposed within or on the subcontainer;

storing the configuration information used for the container in a container database;

repeating steps (a)-(g) for desired sub-containers in the container:

(a) selecting an individual sub-container in the container, (b) collecting a plurality of image data from the biological specimen disposed within or on the sub-container, (c) storing the plurality of image data in an image database, (d) collecting a plurality of feature data from the image data, (e) storing the plurality of feature data in a feature database, (f) calculating a plurality of sub-container summary data using the plurality of image data and the plurality of feature data collected from the biological specimen disposed within or on the sub-container, and (g) storing the plurality of sub-container summary data in a sub-container database;

calculating a plurality of container summary data using the plurality of sub-container summary data from the sub-container database; and storing the plurality of container summary data in the container database.

2. A computer readable medium having stored therein instructions for causing a central processing unit to execute the method of claim 1.

3. The method of claim 1 wherein the biological specimen disposed within or on each subcontainer comprises cells treated with an experimental compound.

4. The method of claim 1 wherein the container comprises a microplate, and each subcontainer comprises a well disposed within the microplate.

5. The method of claim 1 wherein the container database comprises microplate data, the sub-container database comprises well data, the image database comprises photographic image data and the feature database comprises cell feature data.

6. The method of claim 1 wherein the step of collecting a plurality of feature data from the image data comprises collecting any of: size, shape, intensity, texture, location, area, perimeter, shape factor, equivalent diameter, length, width, integrated fluorescence intensity, mean fluorescence intensity, variance, skewness, kurtosis, minimum fluorescence intensity, maximum fluorescence intensity, geometric center, an X-coordinate of a geometric center or a Y-coordinate of a geometric center for cells.

7. The method of claim 1 wherein the step of calculating a plurality of sub-container summary data comprises calculating any of: sizes, shapes, intensities, textures, locations, nucleus area, spot count, aggregate spot area, average spot area, minimum spot area, maximum spot area, aggregate spot intensity, average spot intensity, minimum spot intensit intensity, maximum spot intensity, normalized average spot intensity, normalized spot count, number of nuclei, nucleus aggregate intensity dye area, dye aggregate intensity, nucleus intensity, cytoplasm intensity, difference between nucleus intensity and cytoplasm intensity, nucleus area, cell count, nucleus box-fill ration, nucleus perimeter squared area or nucleus height/width ratio.

8. The method of claim 1 wherein the step of calculating a plurality of container summary data comprises calculating any of: mean size, mean shape, mean intensity, mean texture, locations of cells, number of cells, number of valid fields, standard deviation of nucleus area, mean spot count, standard deviation of spot count, mean aggregate spot area, standard deviation of aggregate spot area, mean average spot area, standard deviation of average spot area, mean nucleus area, mean nucleus aggregate intensity, standard deviation of nucleus intensity, mean dye area, standard deviation of dye area, mean dye aggregate intensity, standard deviation of aggregate dye intensity, mean of minimum spot area, standard deviation of minimum spot area, mean of maximum spot area, standard deviation of maximum spot area, mean aggregate spot intensity, standard deviation of aggregate spot intensity, mean average spot intensity, nuclei intensities, cytoplasm intensities, difference between nuclei intensities and cytoplasm intensities, nuclei areas, nuclei box-fill ratios, nuclei perimeter squared areas, nucleus height/width ratios, well cell counts.

9. The method of claim 1 wherein the container comprises a bio-chip and each subcontainer comprises a micro-gel disposed on the bio-chip.

10. The method of claim 1 further comprising:

storing the container database data and the sub-container database data in a second database on a shared database;

storing the image database and the feature database data in a plurality of third databases on a shared database file server; and creating links in a first database to the second database and the plurality of third databases, wherein the first database includes links to the second database and the plurality of third databases but does not include any data collected from the container, and wherein the first database is used by a display application to view data collected from a container.

11. The method of claim 10 wherein the shared database includes faster access local storage.

12. The method of claim 10 wherein the shared database file server includes slower access remote storage.

13. The method of claim 1 wherein each biological specimen comprises one or more cells.

14. The method of claim 1 wherein the container comprises a DNA array.

15. The method of claim 1 wherein the container comprises a chip based array or a bio-chip based array.

16. A method of collecting experimental data comprising:

storing information about a container in a container database, the container having a plurality of subcontainers disposed therein or thereon, each subcontainer having a biological specimen disposed within or on the subcontainer;

performing steps (a)-(f) for each sub-container:

(a) collecting image data from the biological specimen disposed within or on the subcontainer, (b) storing the image data from the biological specimen in an image database, (c) determining feature data for the biological specimen from the image data, (d) storing the feature data for the biological specimen in a feature database, (e) calculating sub-container summary data using the image data and the feature data associated with the biological specimen disposed within or on the sub-container, and (f) storing the sub-container summary data in a sub-container database;

calculating container summary data using the sub-container summary data for each sub-container associated with the container; and storing the container summary data in the container database.

17. A computer readable medium having stored therein instructions for causing a central processing unit to execute the method of claim 16.

18. The method of claim 16 wherein the container comprises a microplate, and each subcontainer comprises a well.

19. The method of claim 16 wherein each biological specimen comprises one or more cells.

* * * * *

UNITED STATES PATENT AND TRADEMARK OFFICE
CERTIFICATE OF CORRECTION

PATENT NO. : 7,467,153 B2  Page 1 of 1
APPLICATION NO. : 10/649323
DATED : December 16, 2008
INVENTOR(S) : Boyce et al.

It is certified that error appears in the above-identified patent and that said Letters Patent is hereby corrected as shown below:

Title Page
Item 56, References Cited, Other Publications, change "Printed Explorer: Enabling Knowledge - Led R&D Projects, Synomics, www.synomics.com/m/products/productexplorer.htm, pp. 1-3 printed Apr. 9, 2000." To --Project Explorer: Enabling Knowledge - Led R&D Projects, Symonics, www.synomics.com/m/products/projectexplorer.htm, pp. 1-3 printed Apr. 9, 2000.--

Column 11
Line 36, change "step 72" to --step 70--

Column 14
Line 41, change "In such and embodiment" to --In such an embodiment--

Signed and Sealed this

Ninth Day of March, 2010

David J. Kappos
*Director of the United States Patent and Trademark Office*